United States Patent
Yun et al.

(10) Patent No.: US 9,974,818 B2
(45) Date of Patent: May 22, 2018

(54) PPSA AND PSPA POLYMER-VIRUS COMPLEX AND PHARMACEUTICAL COMPOSITIONS COMPRISING THE SAME

(71) Applicant: INDUSTRY-UNIVERSITY COOPERATION FOUNDATION HANYANG UNIVERSITY, Seoul (KR)

(72) Inventors: Chae Ok Yun, Seoul (KR); Kasala Dayananda, Seoul (KR)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 0 days. days.

(21) Appl. No.: 15/235,457

(22) Filed: Aug. 12, 2016

(65) Prior Publication Data
US 2017/0080036 A1 Mar. 23, 2017

(30) Foreign Application Priority Data

Aug. 12, 2015 (KR) ........................ 10-2015-0113754

(51) Int. Cl.
A61K 47/00 (2006.01)
A61K 35/761 (2015.01)
C12N 7/00 (2006.01)
A61K 47/48 (2006.01)
A61K 38/22 (2006.01)
C08G 73/02 (2006.01)

(52) U.S. Cl.
CPC ........ *A61K 35/761* (2013.01); *A61K 38/2221* (2013.01); *A61K 47/48192* (2013.01); *C08G 73/028* (2013.01); *C08G 73/0253* (2013.01); *C12N 7/00* (2013.01); *C12N 2710/10021* (2013.01); *C12N 2710/10032* (2013.01); *C12N 2710/10043* (2013.01)

(58) Field of Classification Search
CPC .............. C08G 73/0253; C08G 73/028; C12N 2710/10032; C12N 2710/10043; A61K 47/00
See application file for complete search history.

(56) References Cited

PUBLICATIONS

Jung et al, Biomacromolecules 16:87-96, 2015; available online Nov. 15, 2014.*
Morris and Sharma, Biomaterials 32:3030-3041, 2011.*
Nam et al, Biomaterials 33:8122-8130, 2012.*
Huang et al, Acta Biomaterialia 6:4285-4295, 2010.*
Kang et al, Biomaterials 32:1193-1203, 2011.*
Kim et al, Biomaterials 31:1865-1874, 2010; available online Dec. 3, 2009.*
Jung et al., "Safety Profiles and Antitumor Efficacy of Oncolytic Adenovirus Coated with Bioreducible Polymer in the Treatment of a CAR Negative Tumor Model", Biomacromolecules 2015, 16:87-96.
Kim et al., "The effect of surface modification of adenovirus with an arginine-grafted bioreducible polymer on transduction efficiency and immunogenicity in cancer gene therapy", Biomaterials 31:1865-1874, 2010).
Jung, "Studies on the transduction efficiency and enhanced antitumor efficacy of adenovirus coated with biodegradable polymer", 2014, Creative Commons, Department of Bioengineering, The Graduate school, Hanyang University.
Untranslated Korean Office Action for application No. 2017-038084793, dated May 31, 2017, 5 pages.

* cited by examiner

*Primary Examiner* — Kevin K Hill
(74) *Attorney, Agent, or Firm* — Swanson & Bratschun, L.L.C.

(57) ABSTRACT

The present invention relates to a complex of PPSA or PSPA polymer and a virus, and a pharmaceutical composition including the same. According to the present invention, when a polymer-virus complex formed using PPSA or PSPA polymer is used, transduction efficiency thereof to cells may be enhanced, an excellent therapeutic effect may thus be obtained when used as a pharmaceutical composition, and, therefore, the pharmaceutical agent may be useful as a therapeutic agent.

9 Claims, 30 Drawing Sheets

[FIG. 1A]
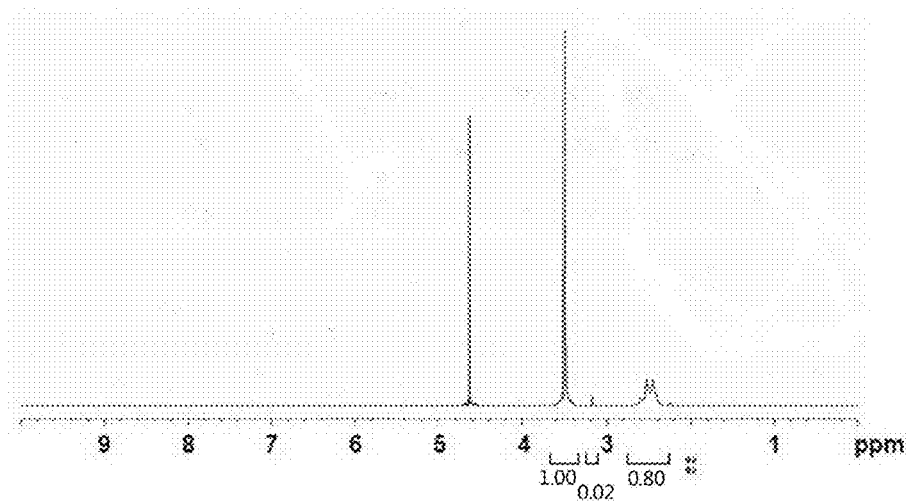
[FIG. 1B]
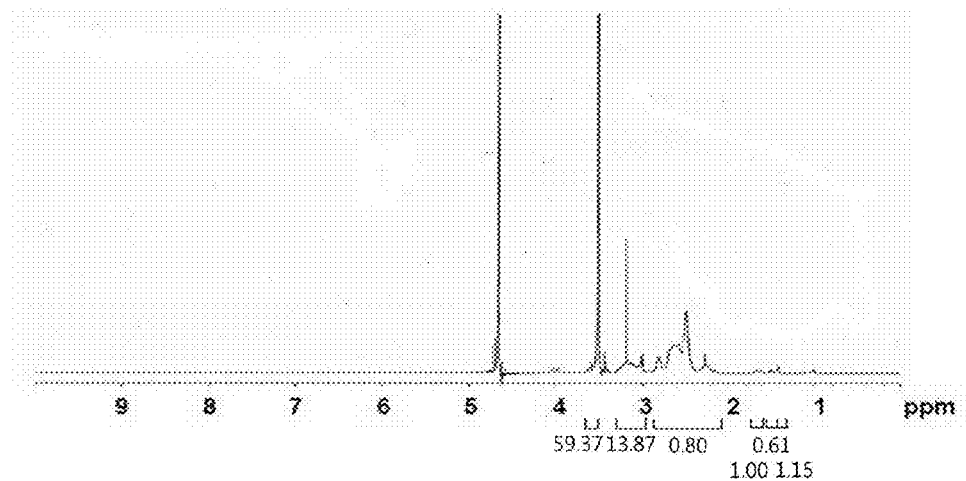

[FIG. 1C]
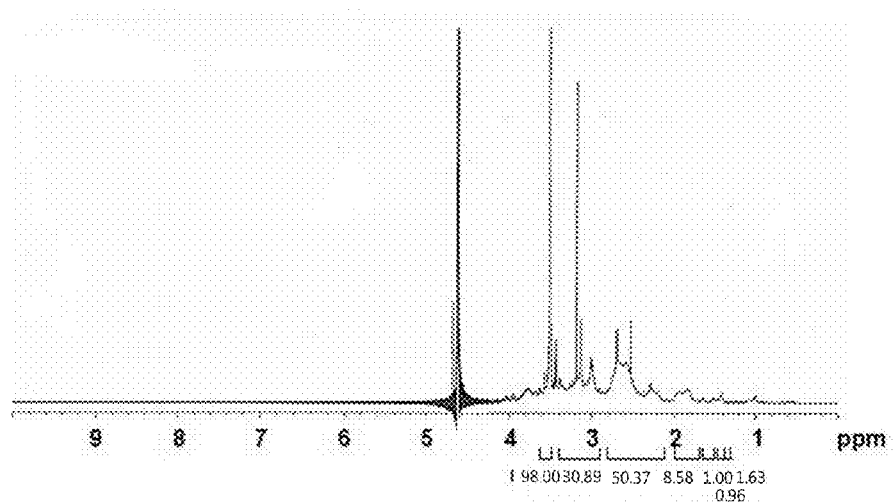
[FIG. 2]
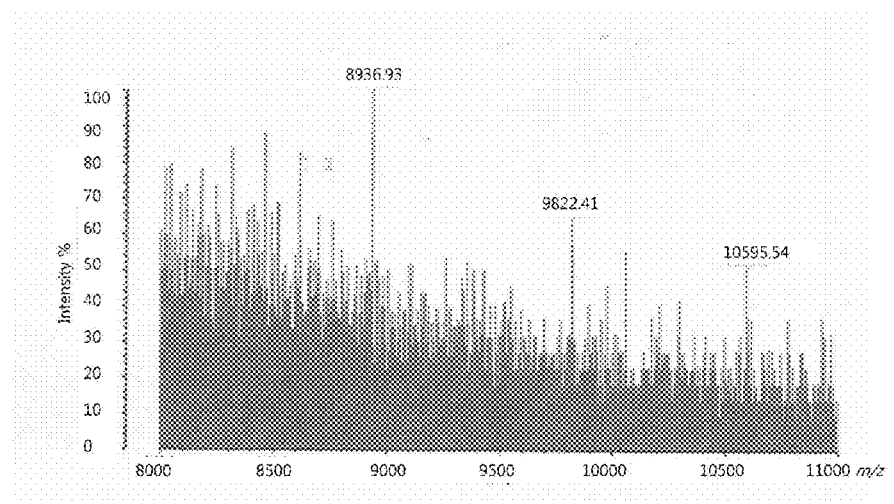

[FIG. 3A]
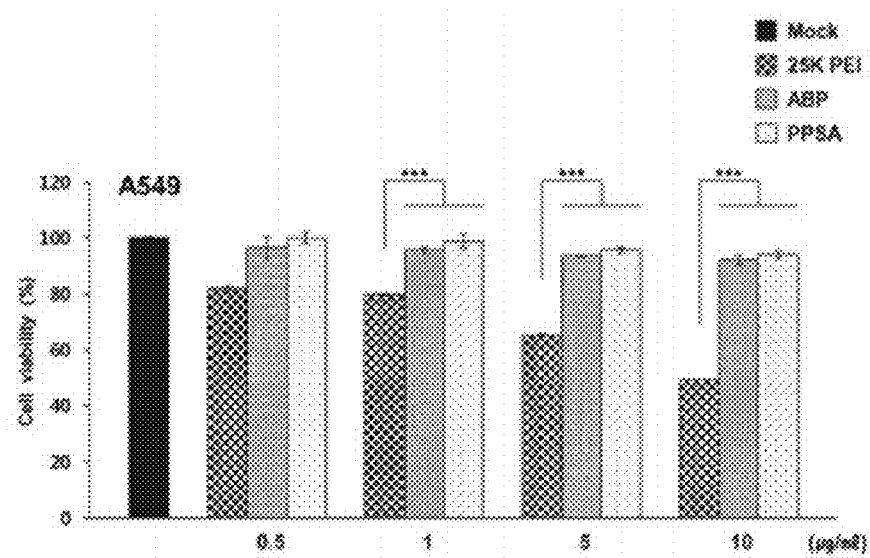
[FIG. 3B]
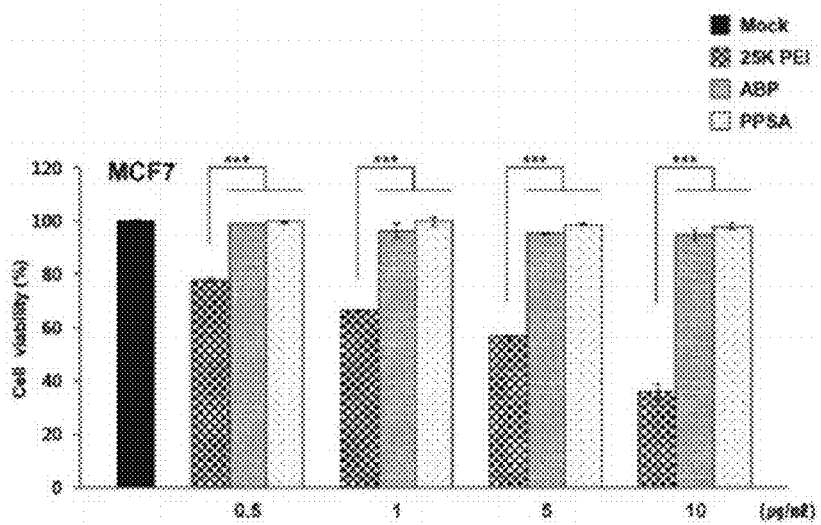

[FIG. 4A]
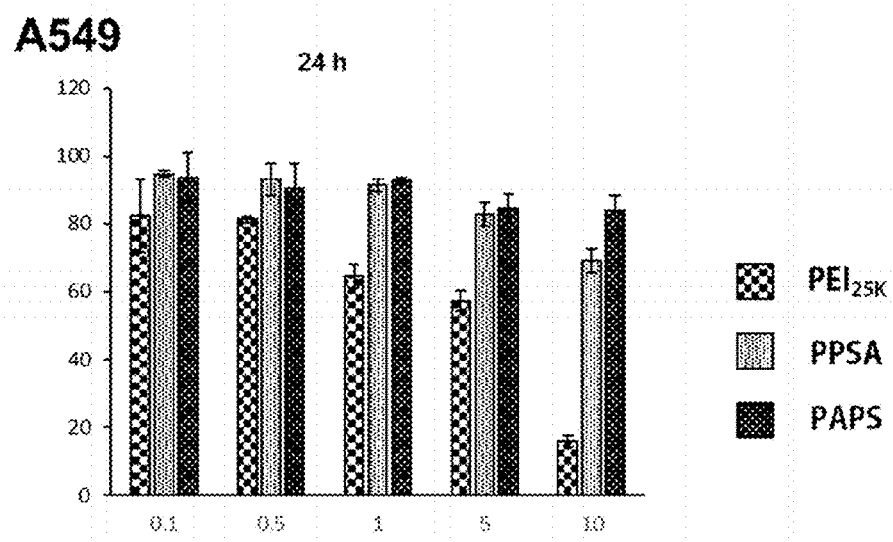
[FIG. 4B]
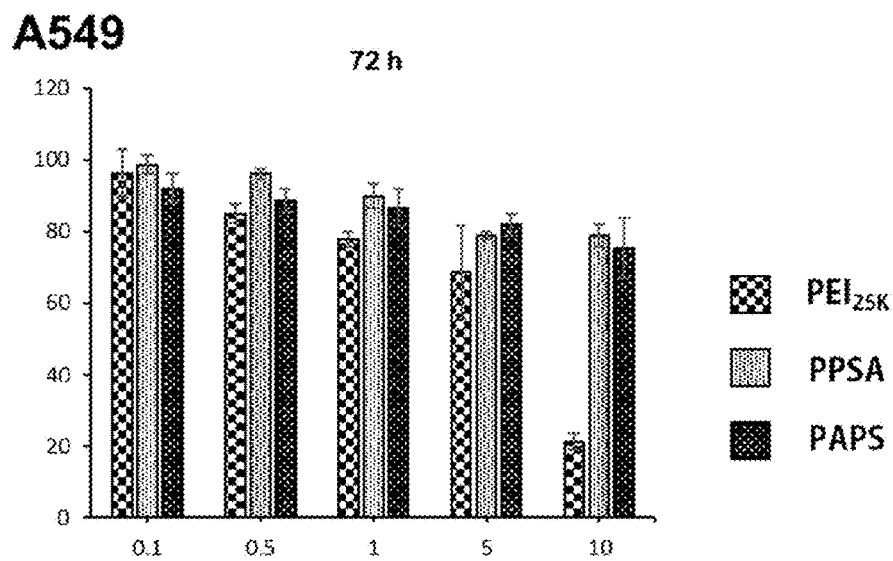

[FIG. 4C]
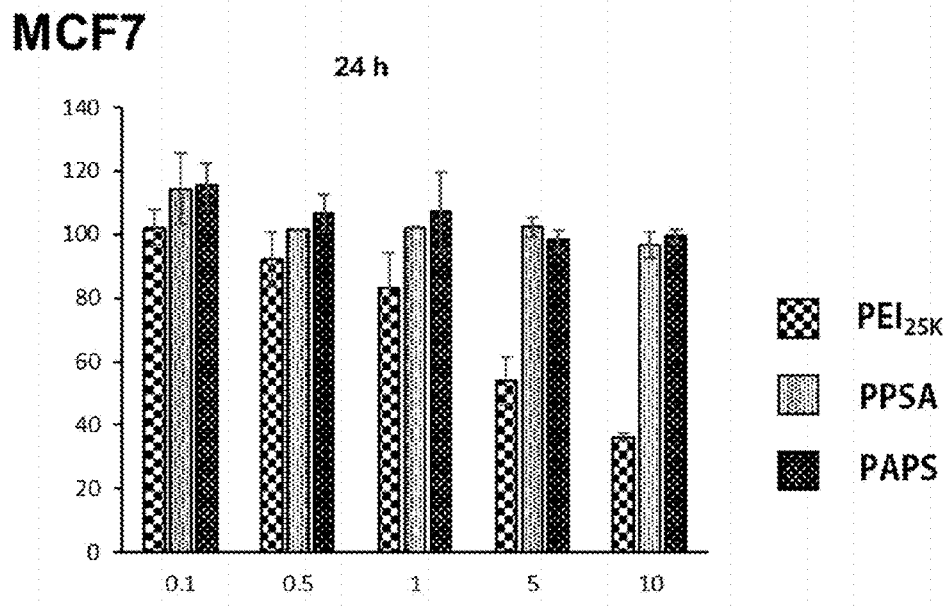
[FIG. 4D]
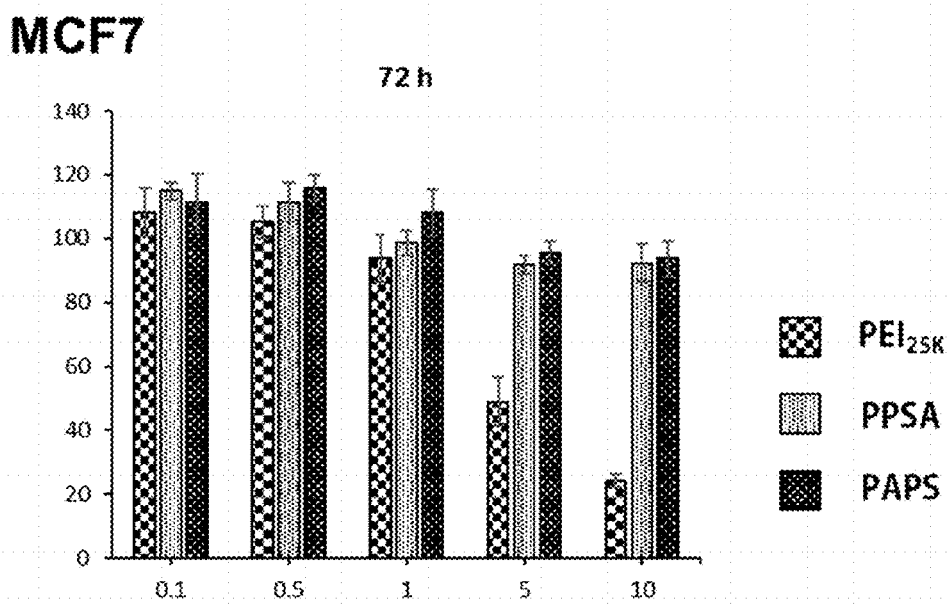

[FIG. 4E]
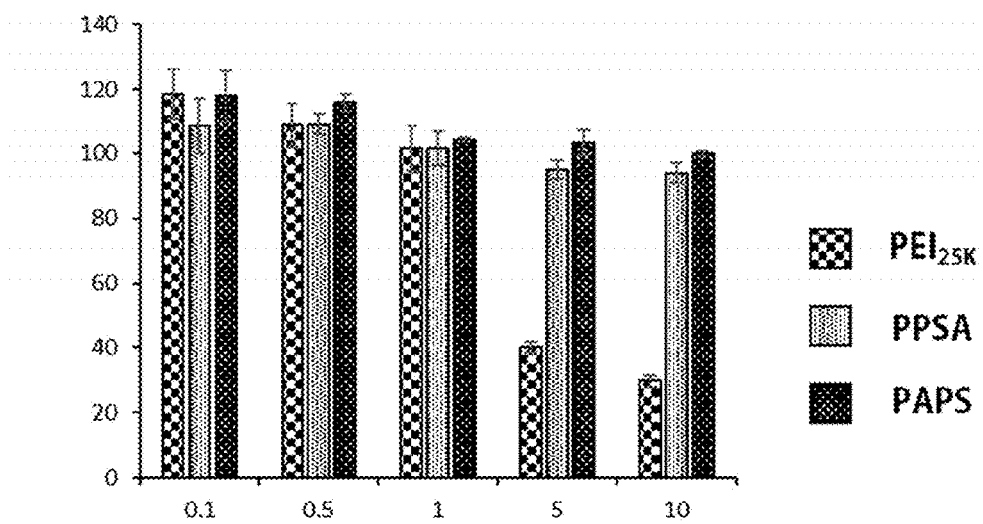
[FIG. 4F]
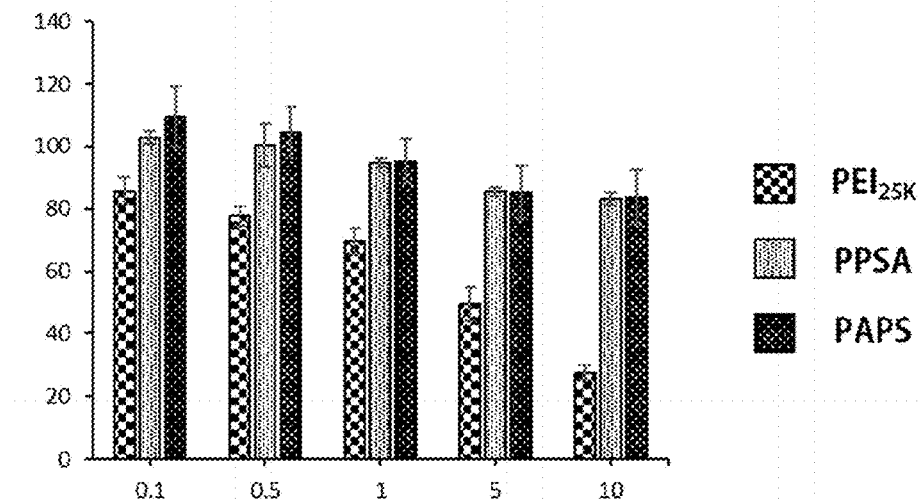

[FIG. 5A]
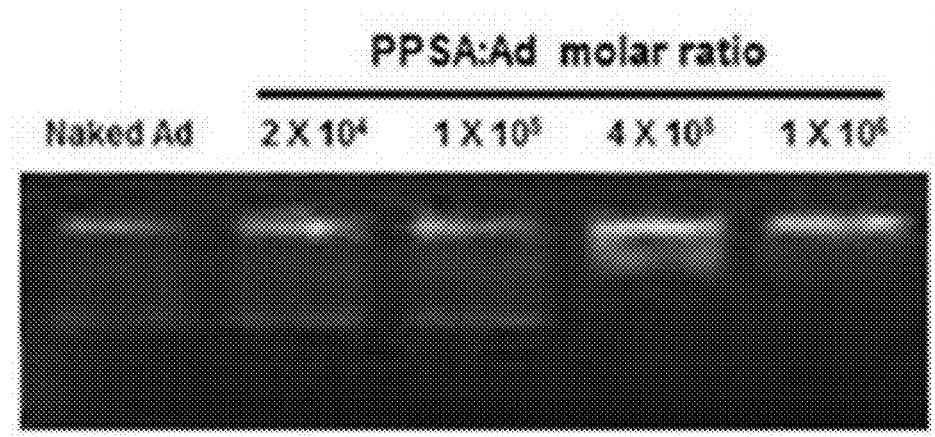
[FIG. 5B]
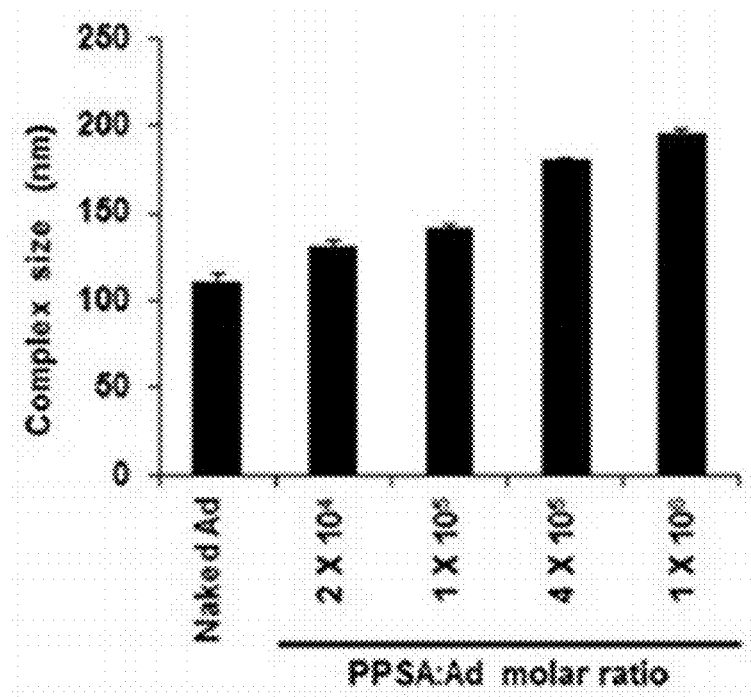

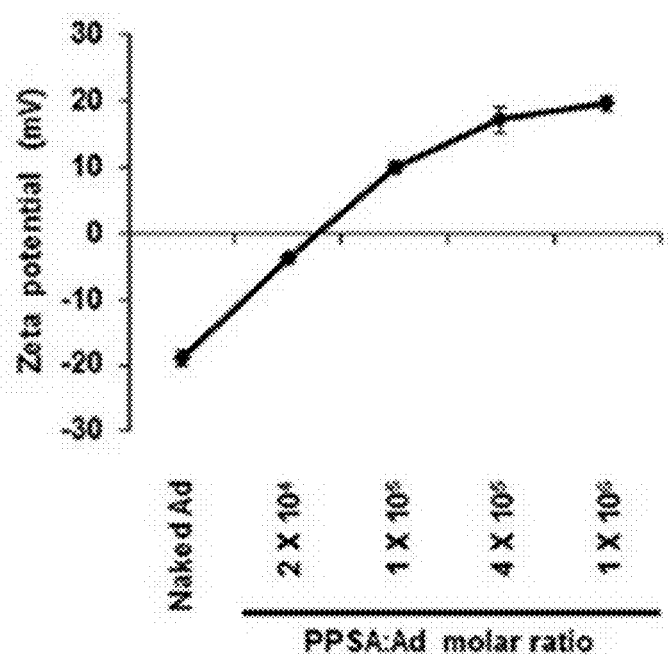
[FIG. 5C]

[FIG. 6A]
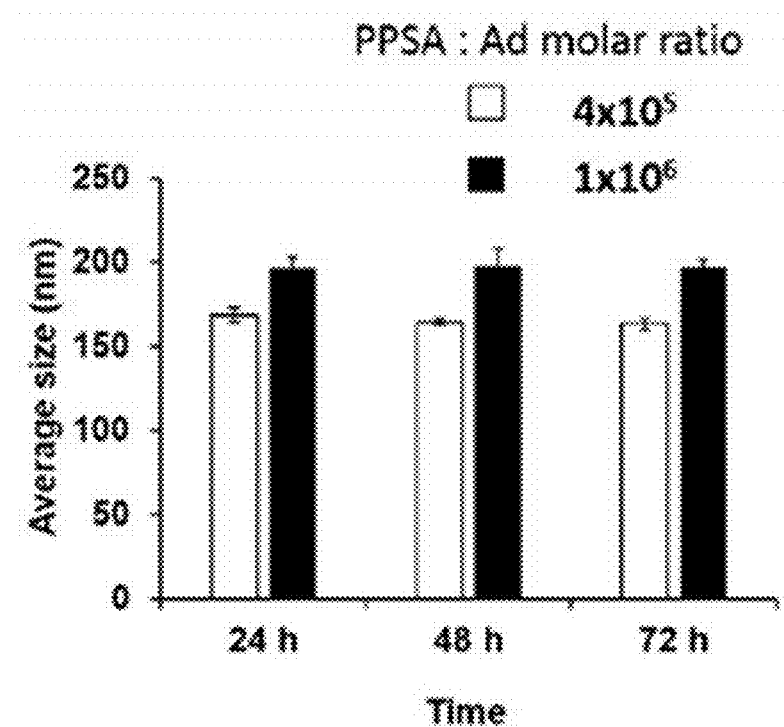

[FIG. 6B]
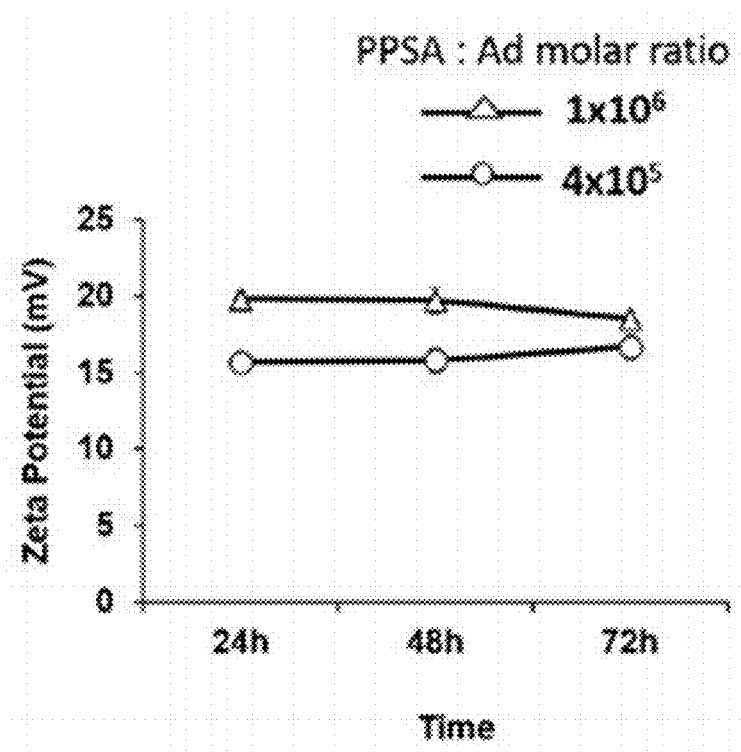

[FIG. 6C]
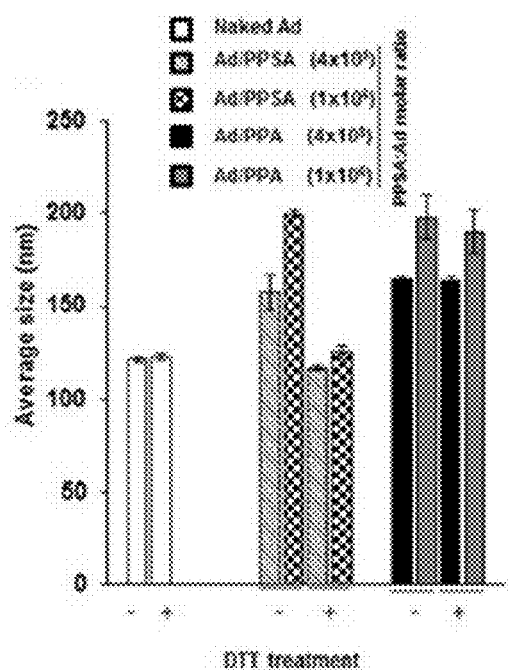
[FIG. 7A]
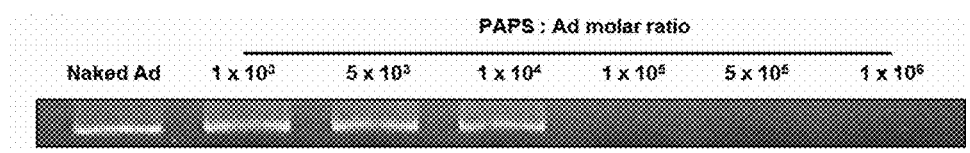

[FIG. 7B]
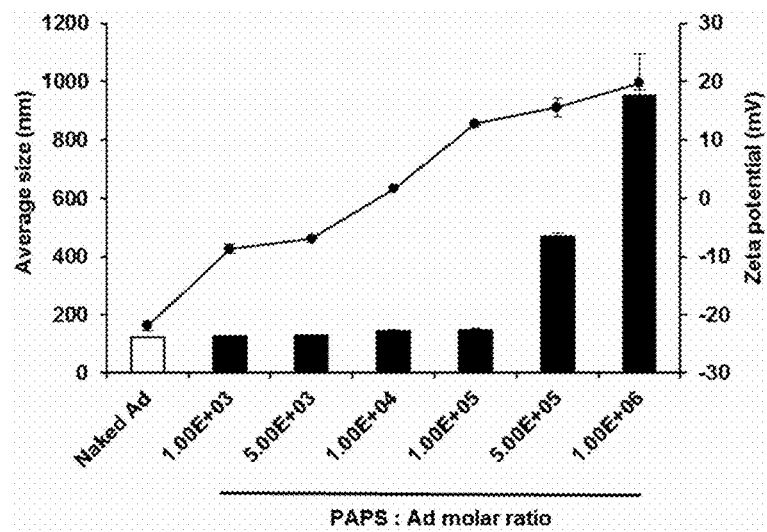
[FIG. 7C]
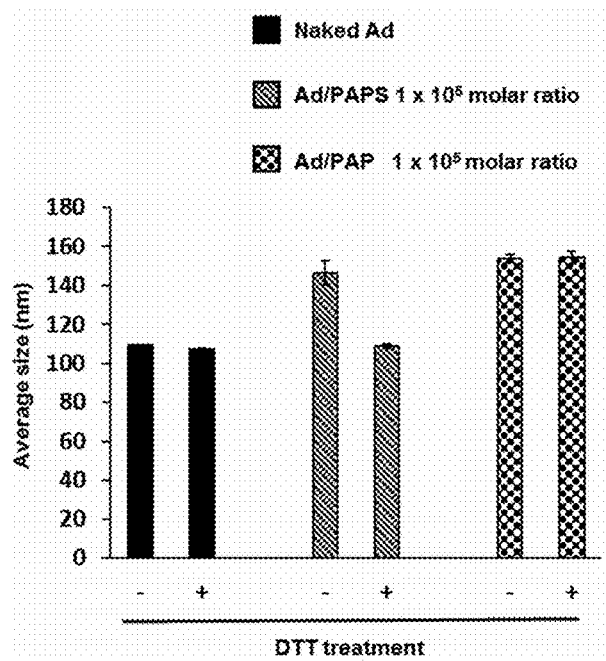

[FIG. 8A]
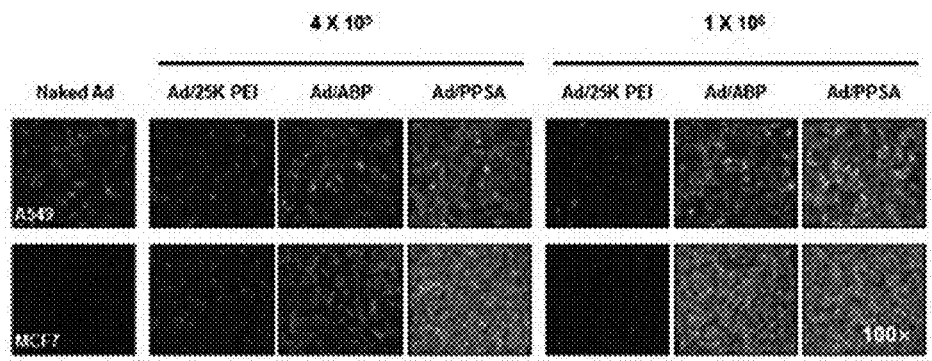
[FIG. 8B]
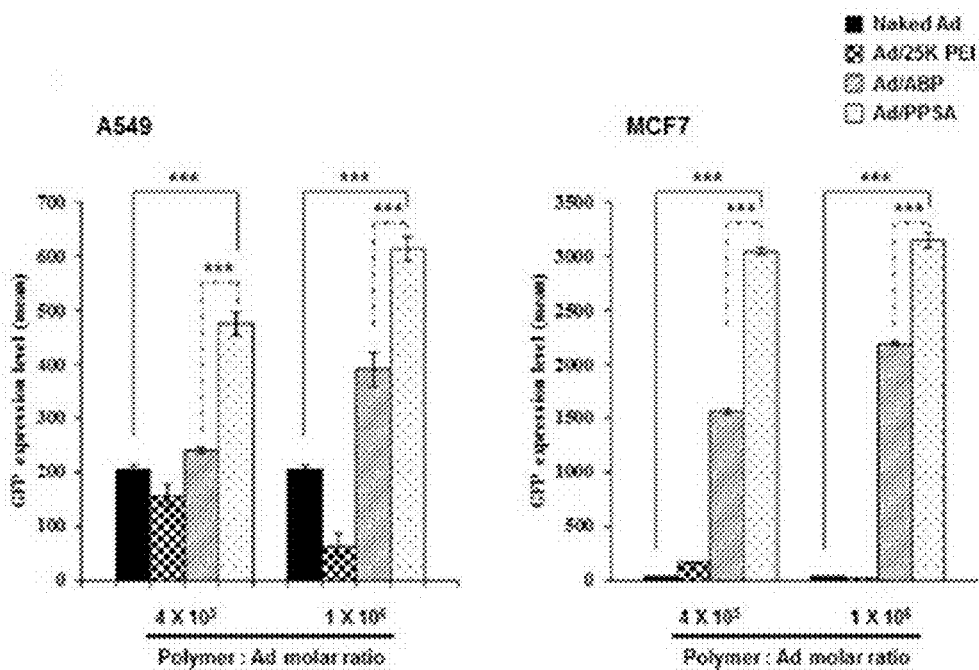

【FIG. 9A】
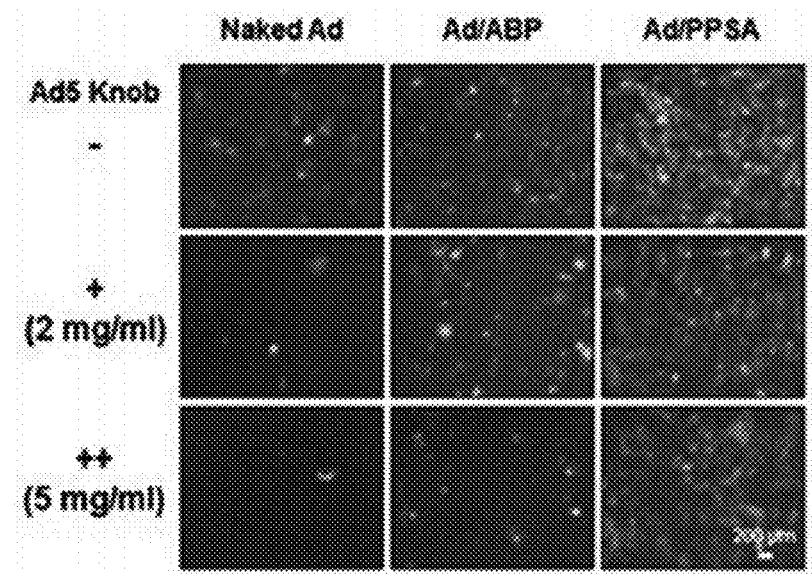
【FIG. 9B】
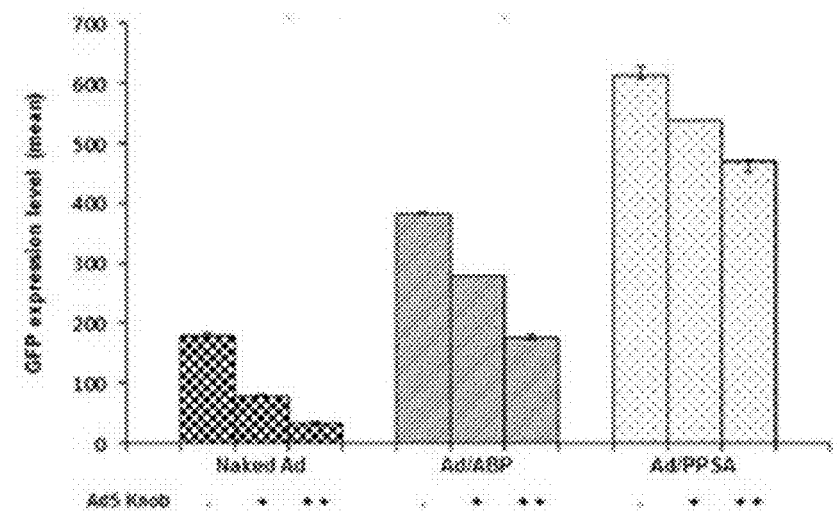

[FIG. 10A]
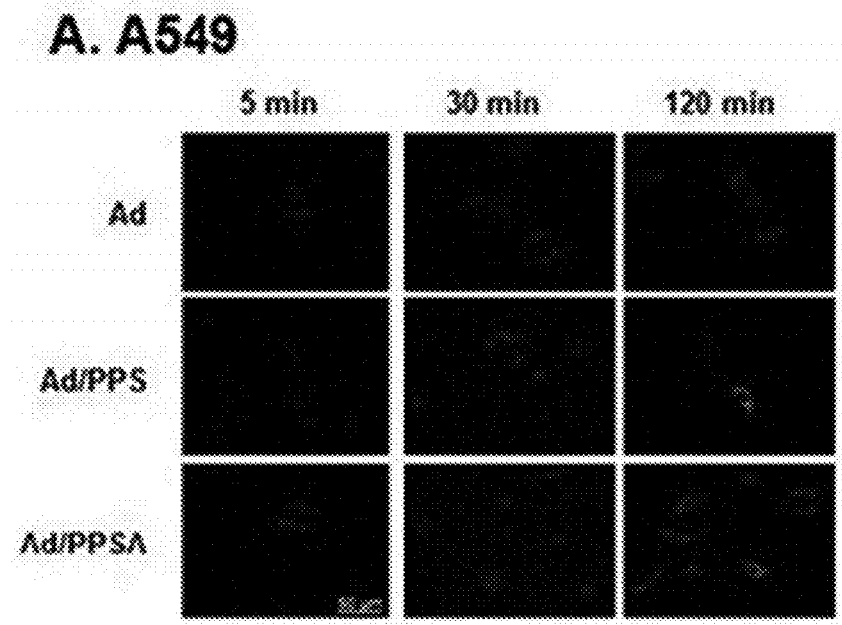
[FIG. 10B]
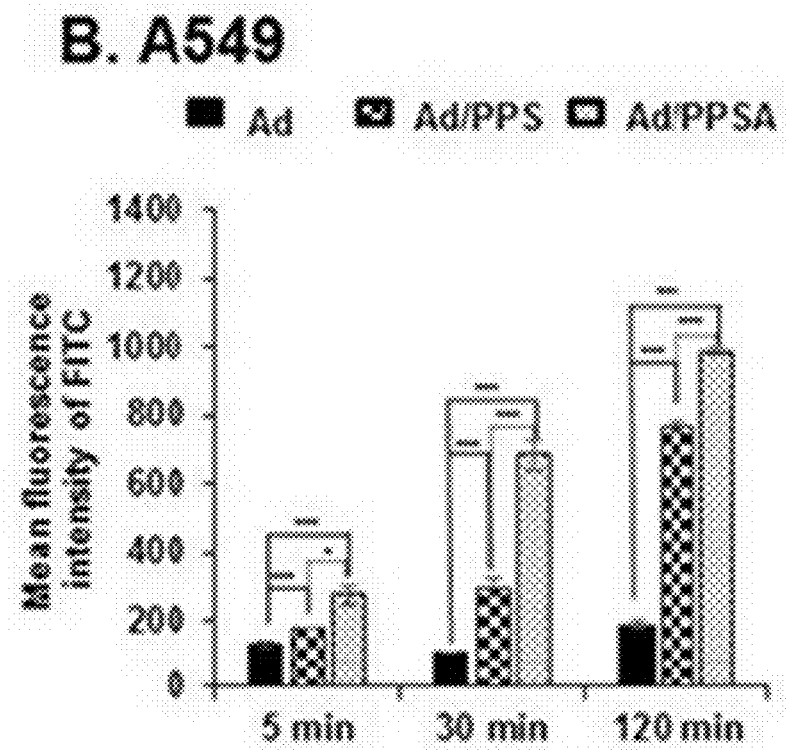

[FIG. 10C]
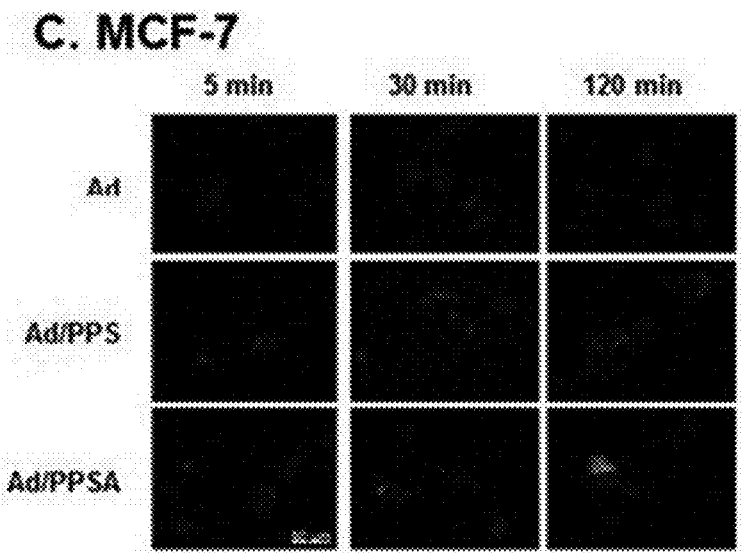
[FIG. 10D]
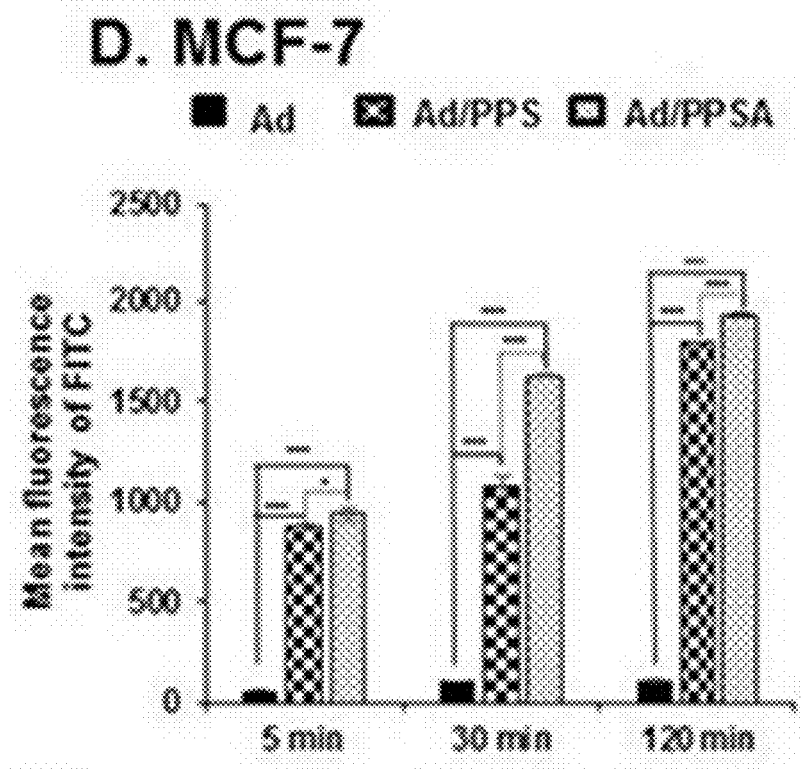

[FIG. 11A]
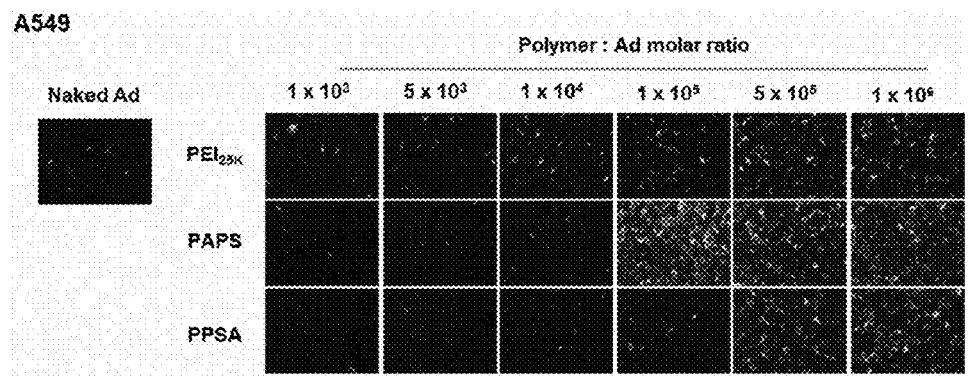
[FIG. 11B]
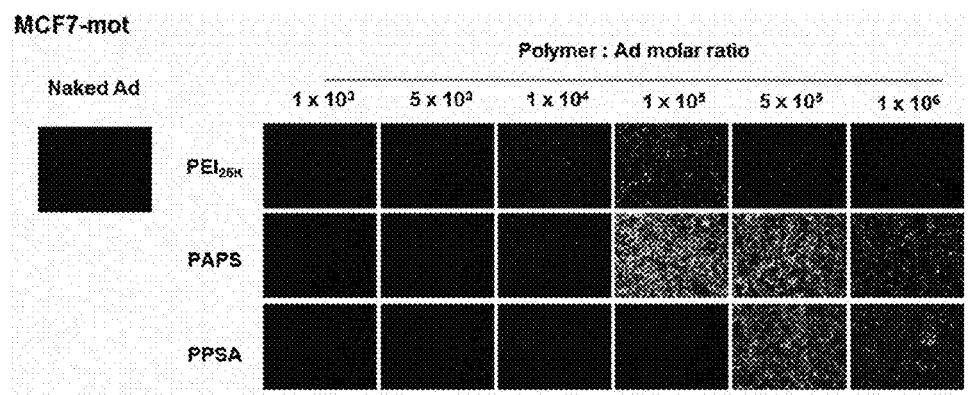

[FIG. 11C]
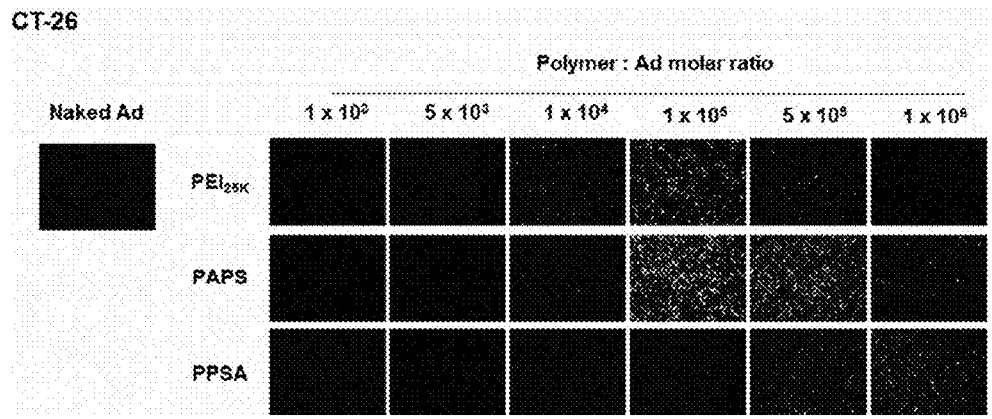
[FIG. 12A]
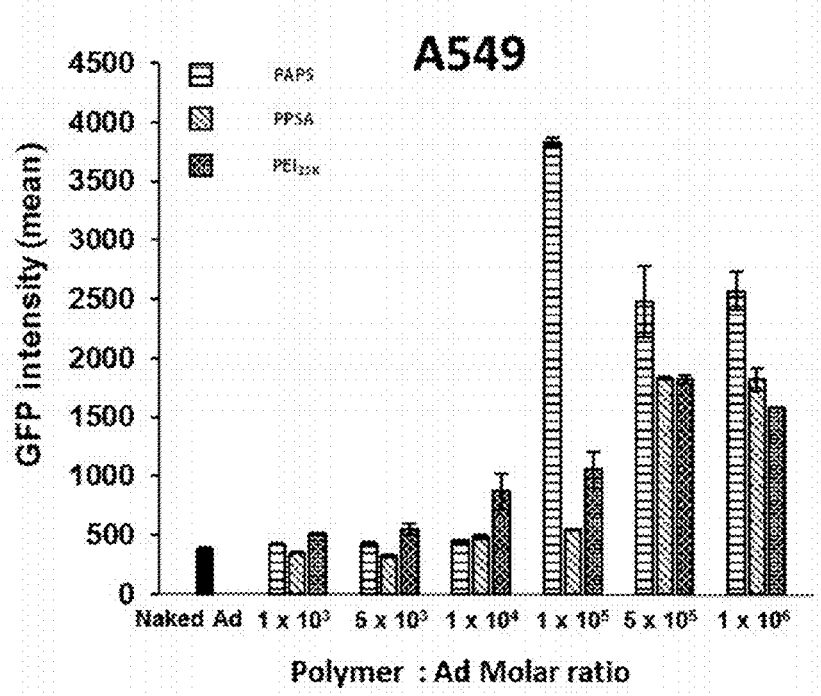

[FIG. 12B]
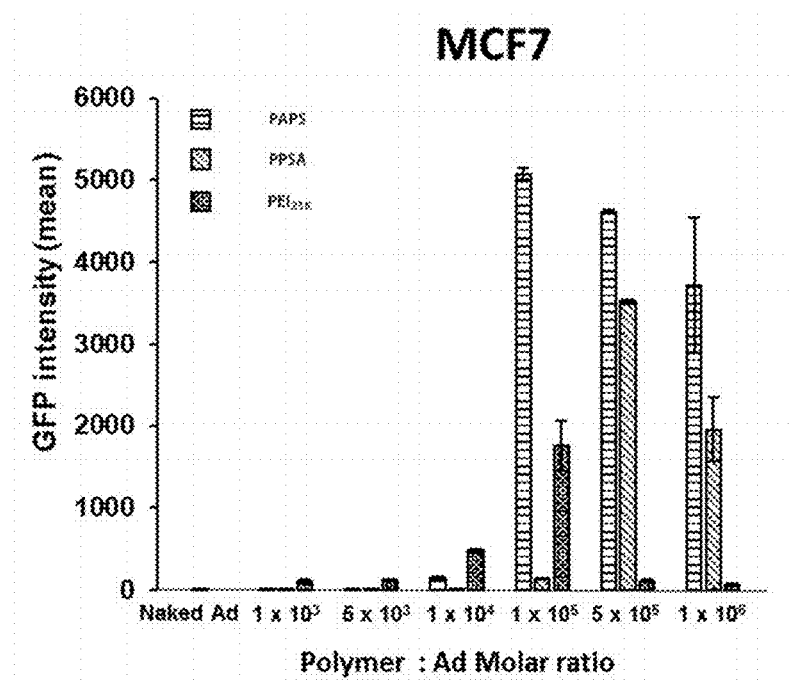

[FIG. 12C]
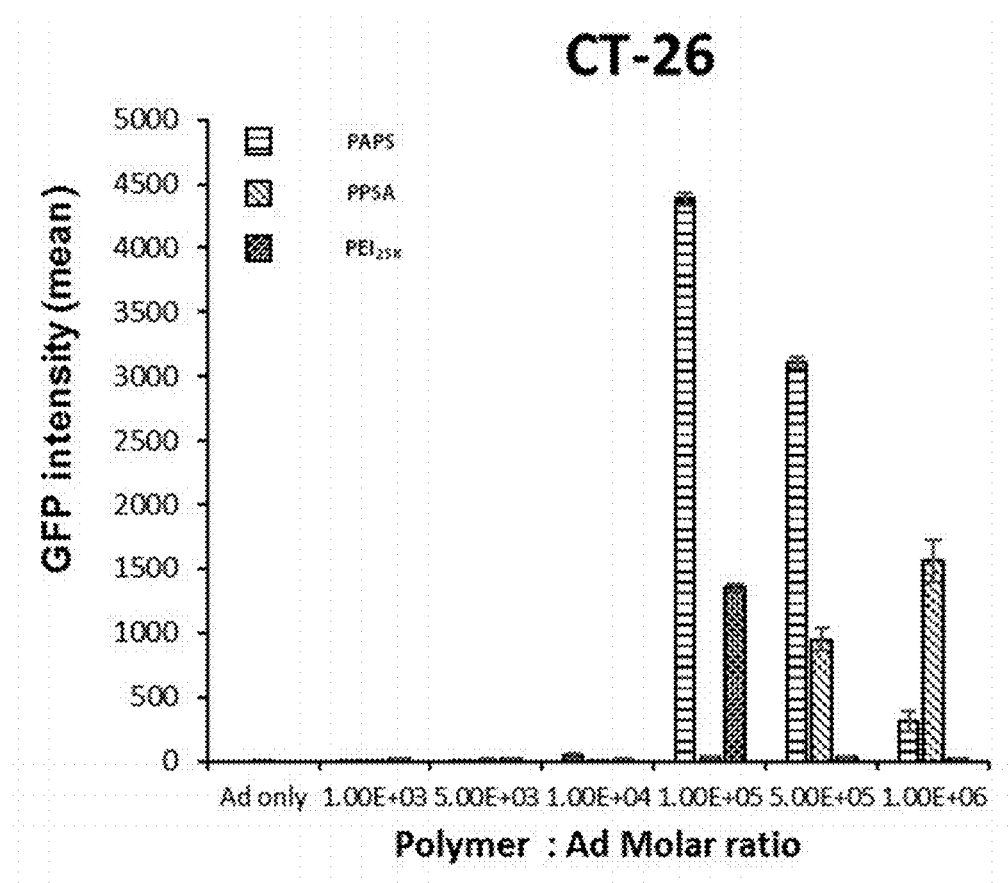

[FIG. 13A]
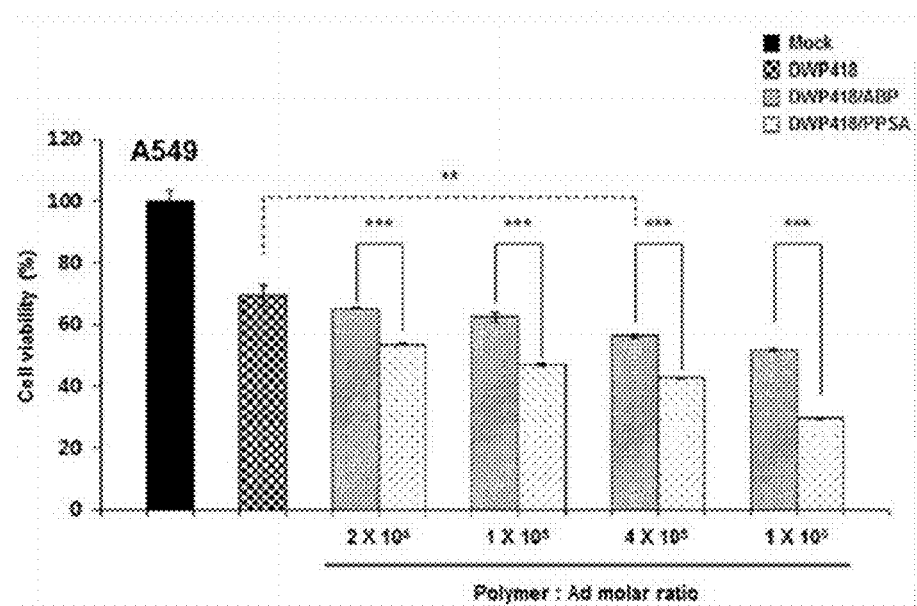
[FIG. 13B]
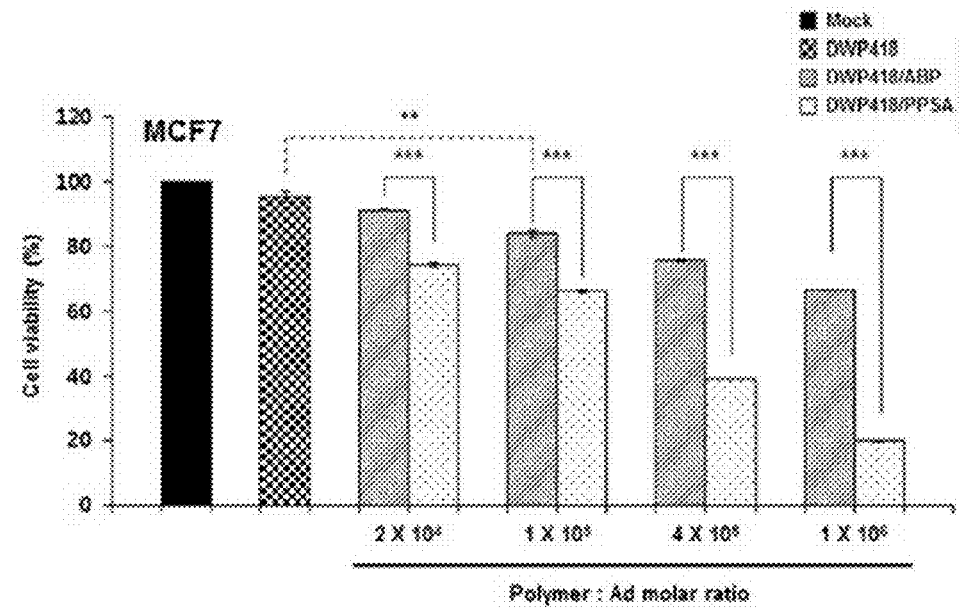

[FIG. 14A]
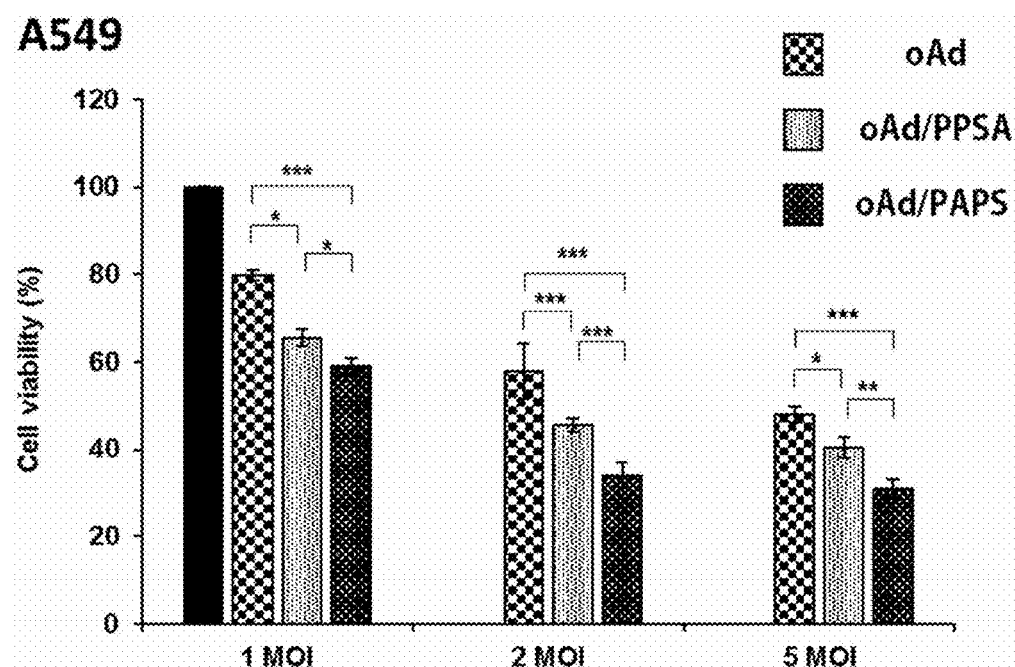

[FIG. 14B]
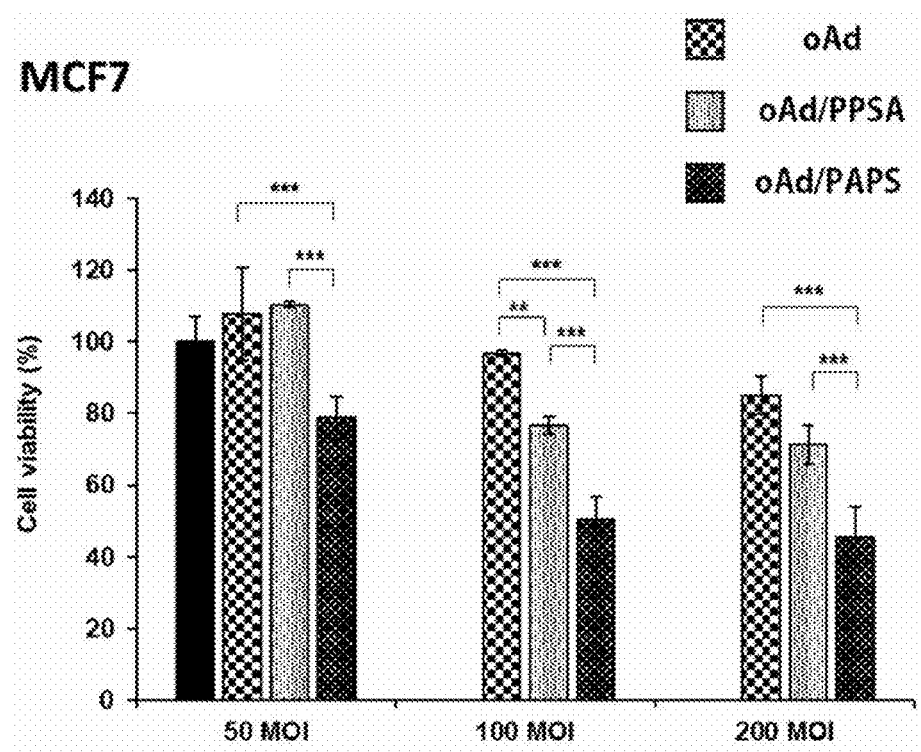

[FIG. 14C]
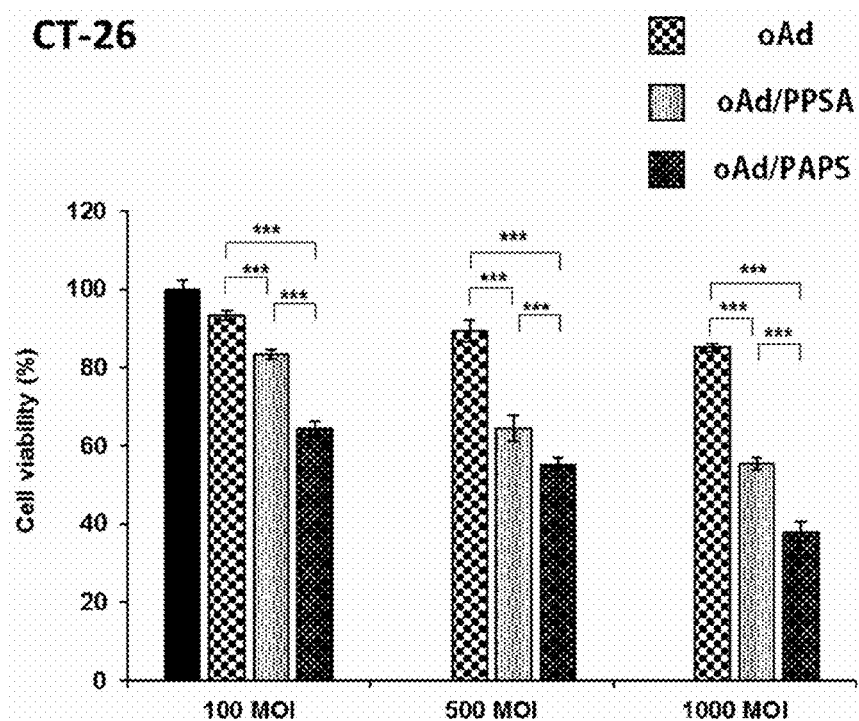

[FIG. 15A]
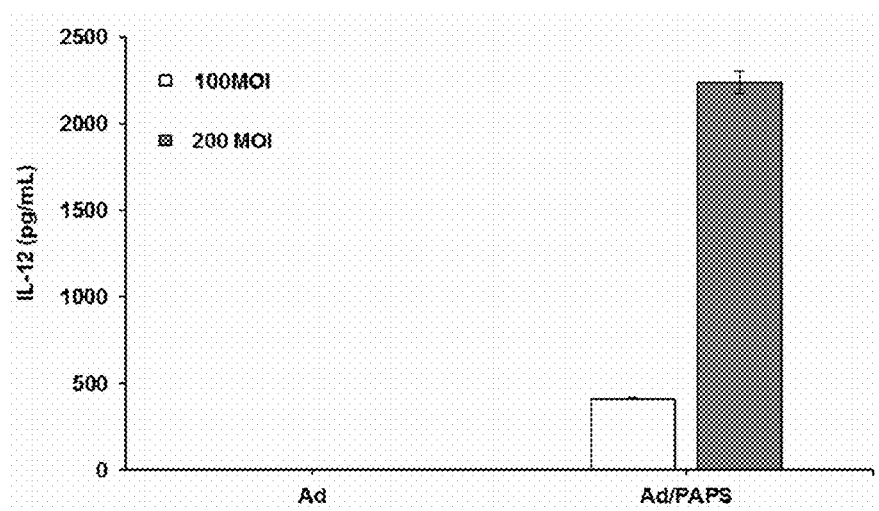
[FIG. 15B]
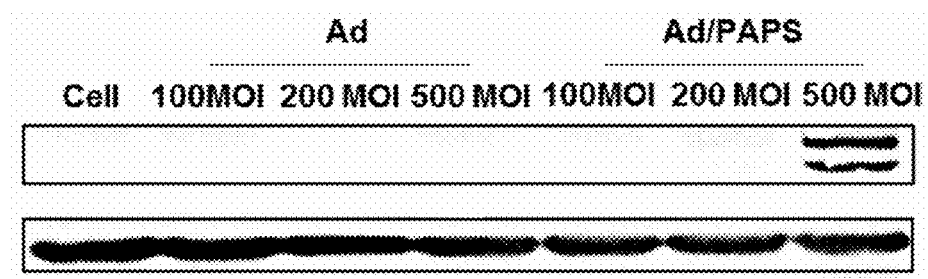

[FIG. 16A]
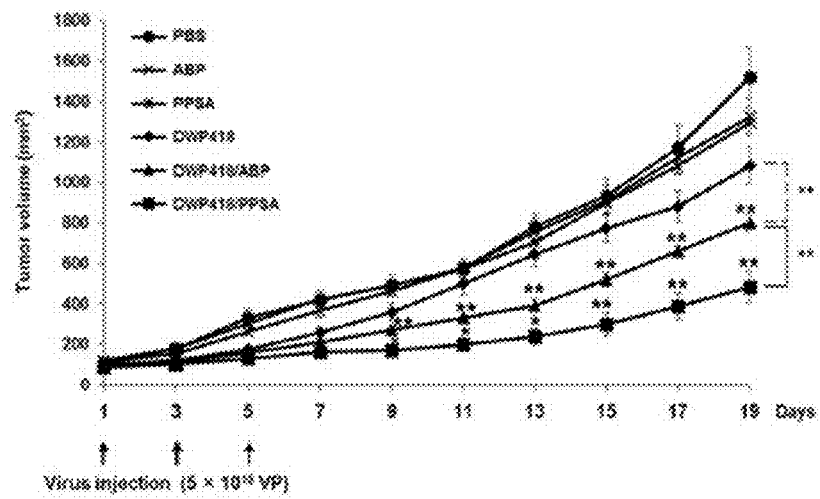
[FIG. 16B]
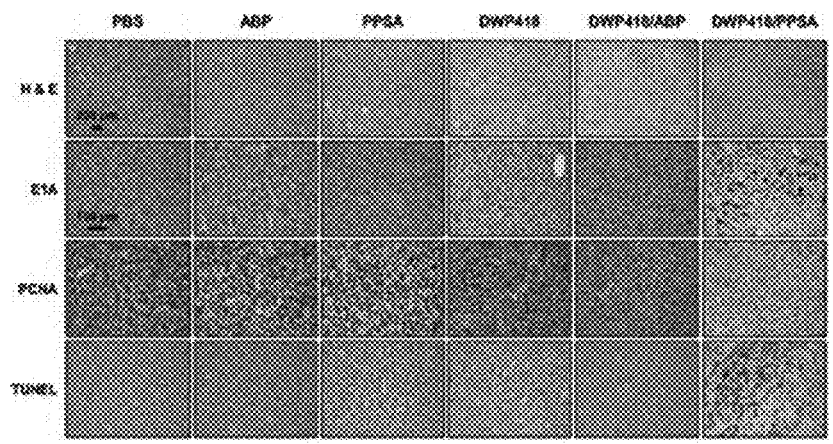

[FIG. 17A]
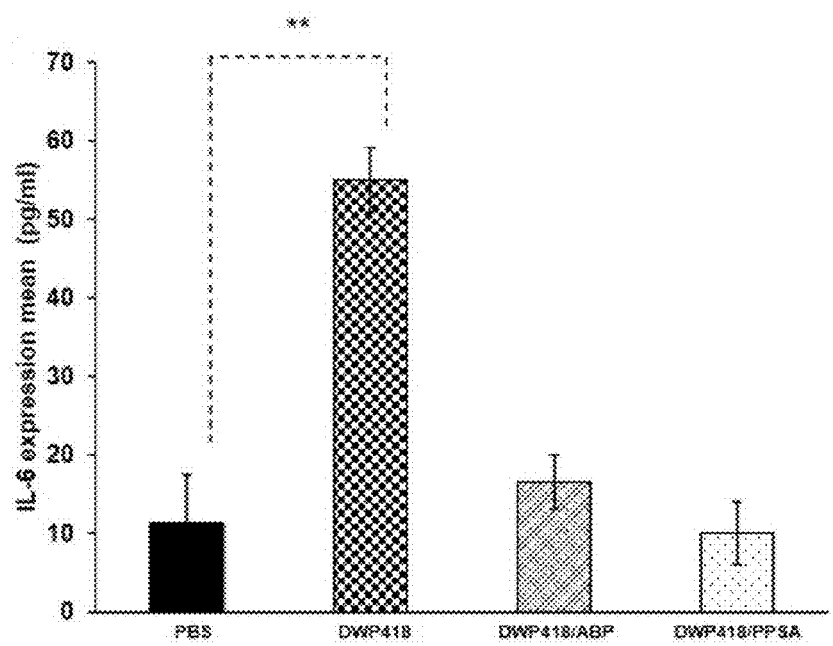

[FIG. 17B]
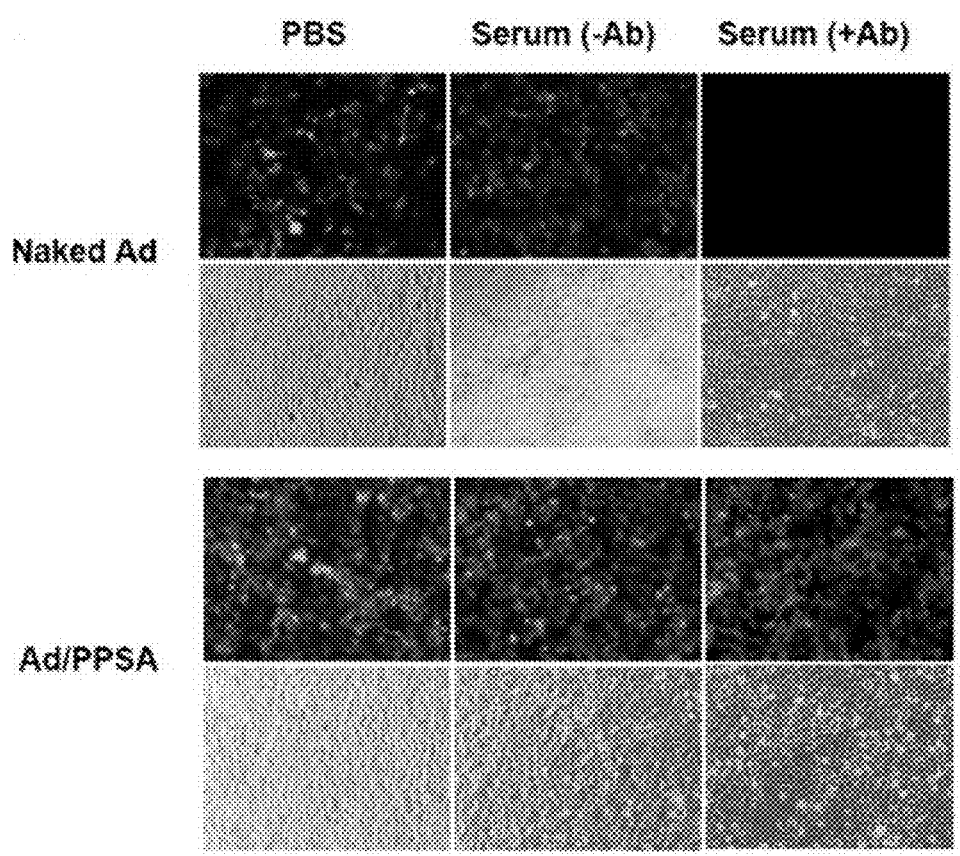

[FIG. 17C]
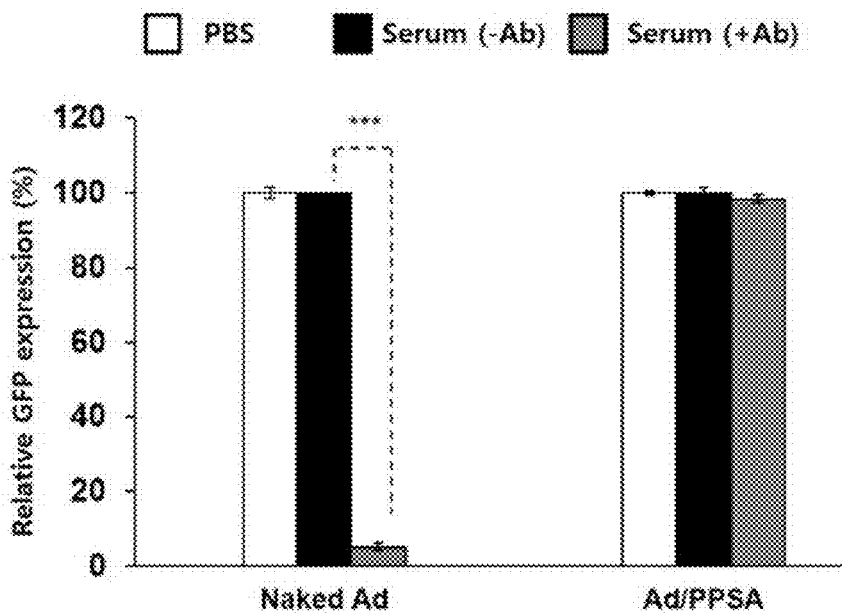
[FIG. 18A]
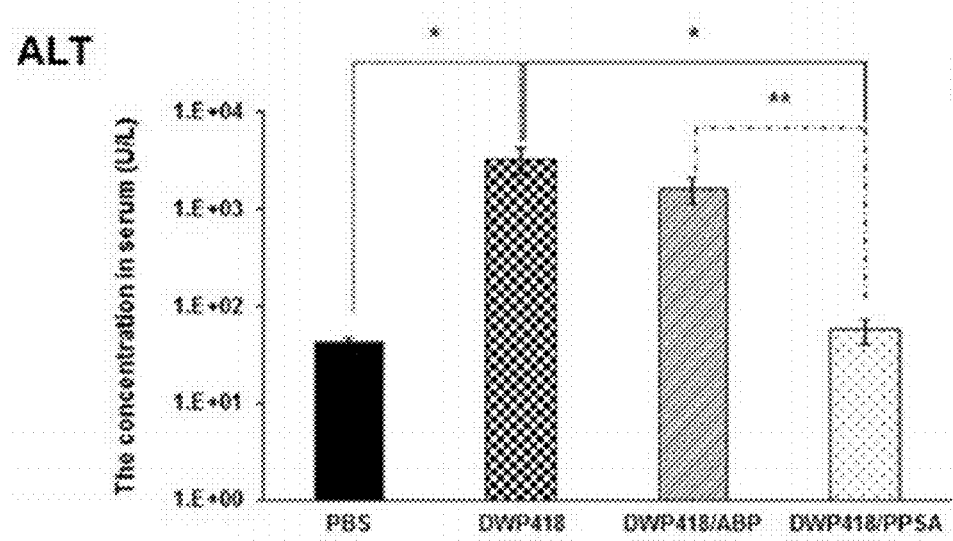

[FIG. 18B]
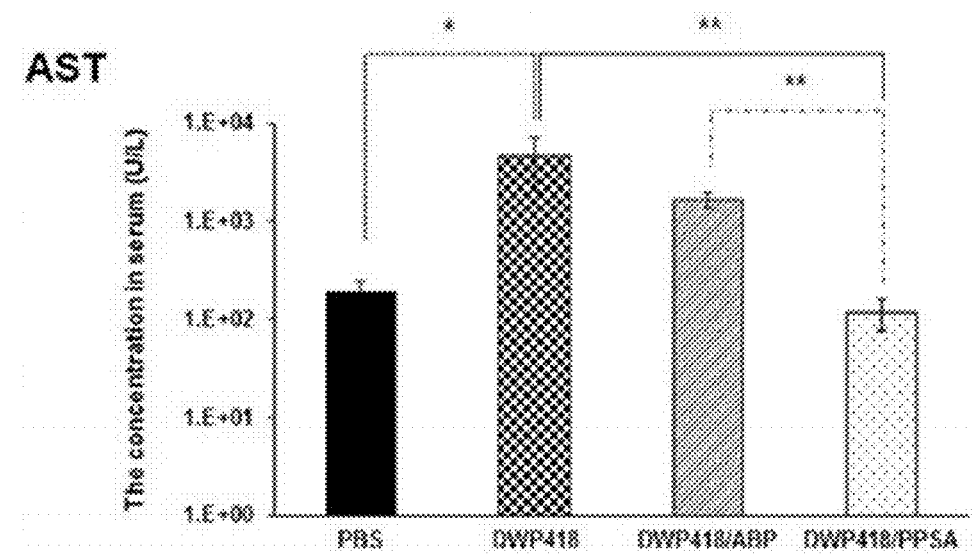

PPSA AND PSPA POLYMER-VIRUS COMPLEX AND PHARMACEUTICAL COMPOSITIONS COMPRISING THE SAME

CROSS-REFERENCE TO RELATED APPLICATION

This application claims priority to and the benefit of Korean Patent Application No. 2015-0113754 filed on Aug. 12, 2015, the disclosure of which is incorporated herein by reference in its entirety.

TECHNICAL FIELD

The present invention relates to a PPSA and PSPA polymer-virus complex, and a pharmaceutical composition including the same as an active ingredient for treating cancer.

BACKGROUND

Over the past two decades, viral and non-viral vectors have emerged as potential delivery systems for cancer gene therapies (1-4). However, each system has a drawback in that biomedical application is limited. For gene therapies, various viral gene transfer systems such as adenoviruses (Ads), lentiviruses, retroviruses and adeno-associated viruses have been studied (5-7). Ads have several unique characteristics such as efficient infection, high loading capacity, and a lack of insertional mutagenesis. As a result, Ads are widely used as a potential anticancer therapy. However, gene transfer using Ads is limited due to dependency on a coxsackievirus and adenovirus receptor (CAR) for transduction (8).

Non-viral vectors have several advantages compared to viral vectors. The non-viral vectors cause low immune responses, have good reproducibility, and have a relatively simple quality control process. As potential, non-viral gene carriers, cationic polymers have been widely investigated. These cationic polymers include polyethylenimine (9-11), poly(amidoamine) (12-16), poly(amino ester) (17) and poly(L-lysine) (18-20).

However, a cationic polymer-based gene transfer system has a drawback of having lower transduction efficiency than a viral gene transfer system. Recently, numerous research on cell penetrating characteristics of cationic arginine (Arg) and Tat peptides having arginine residues have been conducted. Arginine residues can effectively deliver nucleic acids through intracellular translocation (21-24), which is probably caused by the membrane permeability of Arg moieties (25-27). Accordingly, research on modification of various cationic polymers such as chitosan (27), poly(amidoamide), dendrimers (28-31) with arginine residues have been conducted and showed that such polymers have significantly enhanced transduction efficiency compared to unmodified polymers.

In previous research, the inventors attempted to combine non-viral advantages to a viral vector. Accordingly, arginine-grafted, bioreducible polymer (ABP) was produced, and it was confirmed that an ABP and Ad complex (Ad/ABP) has enhanced transduction efficiency and decreased innate immune response, compared to naked Ad (32). However, the size of the complex vector was more than 500 nm which is larger than the ideal size for effective cellular uptake (32). The maximum size for effective cellular uptake through a non-specific, clathrin-dependent process is less than 200 nm.

Therefore, in order to solve such a conventional problem, there is a demand for developing a bioreducible polymer-virus complex which has a size that is less than 200 nm and can be applied in in vivo gene therapy.

Throughout the specification, references are made to numerous theses and patent literature, and citations are represented in parentheses. Disclosures of the cited theses and patent literature are incorporated in its entirety herein by reference to more clearly describe the standard of technology including the present invention and the scope of the present invention.

SUMMARY OF THE INVENTION

The inventors have tried to explore a polymer-virus complex which has a smaller size, enhanced transduction efficiency, and an excellent therapeutic effect compared to a conventional cationic polymer-virus complex. As a result, the inventors found that, when a polymer-virus complex is formed using mPEG-PEI-g-Arg-S-S-Arg-g-PEI-mPEG (PPSA) or PEI-Arg-mPEG-S-S-mPEG-Arg-PEI (PSPA) polymer, the polymer-virus complex exhibits enhanced transduction efficiency and an excellent therapeutic effect and thus completed the present invention.

Therefore, an object of the present invention is directed to providing PPSA (mPEG-PEI-g-Arg-S—S-Arg-g-PEI-mPEG) polymer represented by Formula 1 or PSPA (PEI-Arg-mPEG-S-S-mPEG-Arg-PEI) polymer represented by Formula 2.

Another object of the present invention is directed to providing a polymer-virus complex in which the PPSA or PSPA polymer is bound onto a viral surface.

Still another object of the present invention is directed to providing a pharmaceutical composition including the polymer-virus complex.

Other objects and advantages of the present invention are more clearly explained by detailed descriptions, claims, and drawings of the present invention as below.

DETAILED DESCRIPTION OF THE INVENTION

In one aspect of the present invention, the present invention provides PPSA polymer represented by Formula 1 below.

[Formula 1]
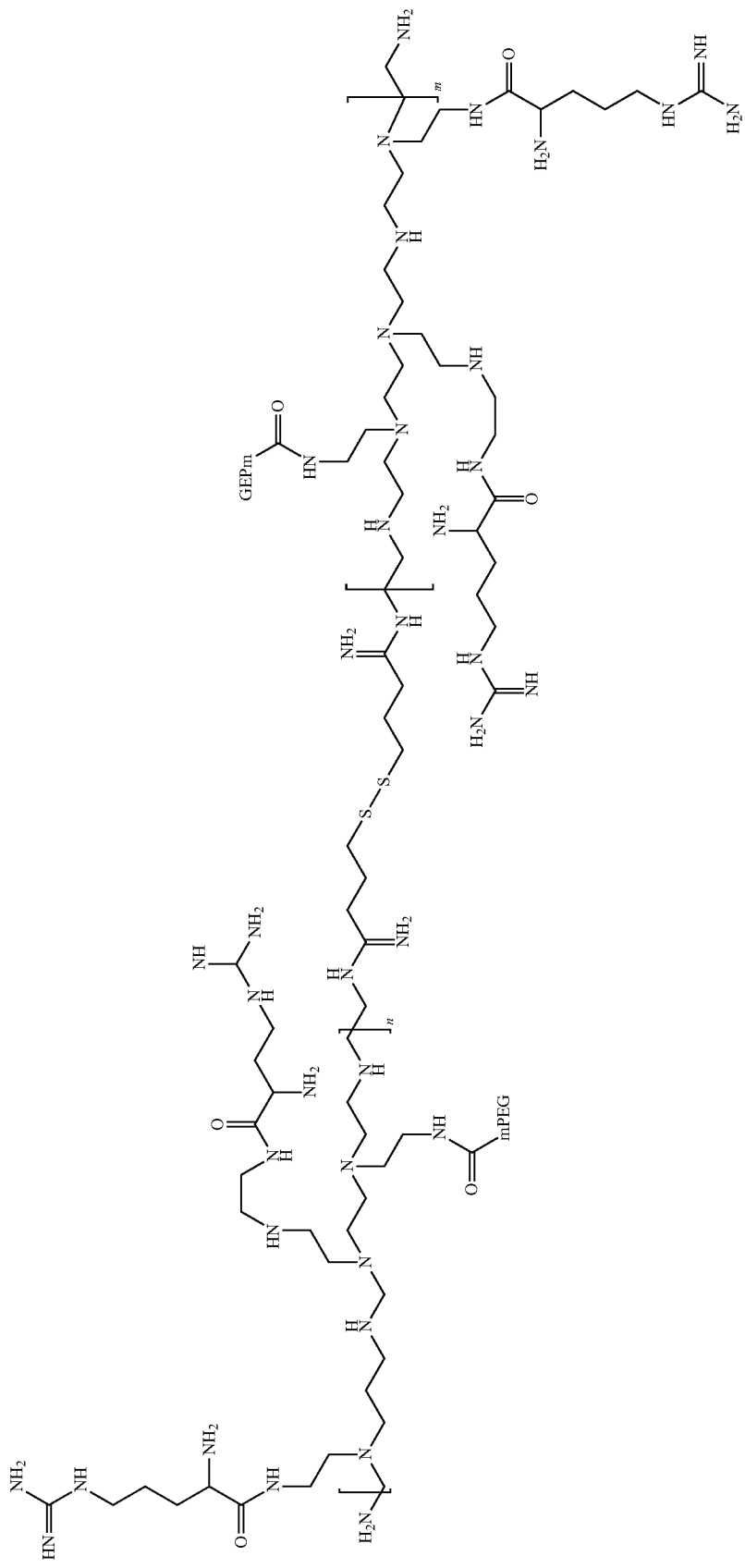

In Formula 1, each of n and m independently is an integer from 1 to 5.

According to an exemplary embodiment of the present invention, in Formula 1, n and m may each independently be 1.

A process of synthesizing the PPSA polymer will be simply described as follows:

First, mPEG-PEI was synthesized by reacting polyethyleneimine (PEI) 1.8 kDa and succinimidyl ester methoxy polyethylene glycol (mPEG-NHS). Subsequently, to synthesize mPEG-PEI-g-Arg, arginine was grafted onto the polymer. Afterward, to synthesize mPEG-PEI-g-Arg-SH, the mPEG-PEI-g-Arg was treated with imidothiolane to link a thiol group. Finally, a new bioreducible polymer, mPEG-PEI-g-Arg-S-S-Arg-PEI-mPEG (PPSA), was synthesized by linking a terminal thiol group by disulfide bonding.

In another aspect of the present invention, the present invention provides PSPA polymer represented by Formula 2. The PSPA polymer is also called a PAPS polymer, and thus in the specification, both the PSPA polymer and the PAPS polymer may be used.

complex in which the polymer is bound to a viral surface. Specifically, the present invention may provide a polymer-virus complex in which PPSA polymer of Formula 1 or PSPA polymer of Formula 2 is bound to a viral surface.

According to an exemplary embodiment of the present invention, it was confirmed that the polymer-virus complex has a smaller size, enhanced transduction efficiency and a higher therapeutic effect than a conventional cationic polymer-virus complex. Accordingly, the polymer-virus complex increases efficiency of delivering a pharmaceutically active ingredient to a cell, thereby exhibiting an excellent therapeutic effect, and thus can be used in treating, preventing and improving various diseases of all kinds by changing pharmaceutically active ingredient for a target disease.

The virus used in the polymer-virus complex of the present invention may be any type of virus, specifically, a virus which is included in a therapeutic agent, a vaccine, a drug delivery system, a vector, or a gene carrier for being used in treatment of a disease. For example, the virus may be any one selected from the group consisting of Ads, adeno-associated viruses (AAVs), retroviruses, lentiviruses,

[Formula 2]

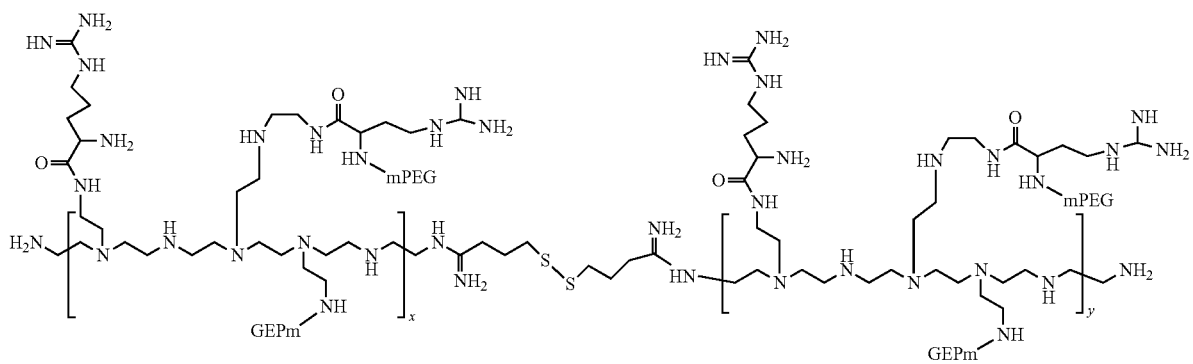

In Formula 2, each of x and y independently is an integer from 1 to 5.

According to an exemplary embodiment of the present invention, in Formula 2, x and y may each independently be 1.

A process of synthesizing the PSPA polymer will be simply described as follows:

First, polyethylenimine (PEI) was treated with arginine to synthesize PEI-Arg. Then, to synthesize PEI-Arg-mPEG, the PEI-Arg was treated with succinimidyl ester methoxy poly(ethylene glycol) (mPEG-NHS). Afterward, to synthesize PEI-Arg-mPEG-SH, the PEI-Arg-mPEG was treated with imidothiolane to link a thiol group. Finally, a new bioreducible polymer, PEI-Arg-mPEG-S-S-mPEG-Arg-PEI (PSPA), was synthesized by linking a terminal thiol group by disulfide bonding.

A chargeable portion of the PPSA or PSPA polymer of the present invention provides positive charges to the polymer at in vivo pH, and specifically, at approximately neutral pH so as to be bound to a viral surface (i.e., a negatively charged adenovirus surface) by ionic interactions.

When a bioreducible portion having disulfide bonds is reduced in an in vivo acidic environment, the disulfide bond is converted into SH groups, and thus the polymer structure is disrupted, resulting in releasing naked viruses.

For this reason, according to an aspect of the present invention, the present invention provides a polymer-virus herpes simplex viruses and vaccinia viruses, but the present invention is not limited thereto.

According to an embodiment of the present invention, it was experimentally confirmed that a complex in which the PPSA polymer or PSPA polymer is bound to an adenoviral surface has excellent transduction efficiency and an excellent therapeutic effect.

i. Adenoviruses (Ads)

Adenoviruses (Ads) are widely used as gene transfer vectors due to medium genome size, convenient manipulation, a high titer, a wide range of target cells, and excellent infectivity. Both ends of a genome include 100 to 200 bp inverted terminal repeats (ITRs), which are cis-elements crucial for DNA replication and packaging. E1 regions (E1A and E1B) of a genome encode proteins for replication and regulating the replication of genes of a host cell. E2 regions (E2A and E2B) encode protein involved in viral DNA replication.

Among adenoviral vectors that have been developed so far, E1 region-deleted replication deficient adenoviruses are widely used. Meanwhile, E3 regions are removed from conventional adenoviral vectors, thereby providing foreign gene-inserted sites (Thimmappaya, B. et al., *Cell*, 31:543-551 (1982); and Riordan, J. R. et al., *Science*, 245:1066-1073 (1989)). Meanwhile, a target nucleotide sequence to be delivered into a cell is inserted into, specifically, deleted E1 regions (the E1A region and/or the E1B region, and preferably, the E1B region) or E3 regions and, more specifically, inserted into the deleted E1 regions.

The term "deletion" used herein in relation to a genome sequence refers to not only complete deletion of a corresponding sequence but also partial deletion.

Also, Ads are possible to package up to approximately 105% of a wild-type genome, and therefore approximately 2 kb may be additionally packaged (Ghosh-Choudhury et al., *EMBO J.*, 6:1733-1739 (1987)). Thus, the above-described foreign sequence inserted into the adenovirus may be additionally bound to the genome of the adenovirus.

Ads have 42 different serotypes and subgroups A to F. Among these, Ad type 5 included in subgroup C is the most suitable start material for obtaining adenoviral vectors of the present invention. Biochemical and genetic information of the Ad type 5 are well known.

The foreign gene delivered by the adenovirus is replicated by the same method as an episome, and thus it has very low genetic toxicity against the host cells.

ii. Retroviruses

Retroviruses are widely used as gene transfer vectors since they can insert their genes into a host genome, deliver a great quantity of foreign genetic materials, and have a broad spectrum of cells that can be infected.

To construct a retroviral vector, a target nucleotide sequence to be delivered, instead of a retroviral sequence, is inserted into a retroviral genome, thereby producing a replication-defective virus. To produce virions, a packaging cell line having gag, pol and env genes, but not having long terminal repeats (LTRs) or ψ sequence, is constructed (Mann et al., *Cell,* 33:153-159 (1983)). When a recombinant plasmid including a desired nucleotide sequence to be delivered, LTR and ψ sequences are introduced into the cell line, the ψ sequence allows the production of an RNA transcript of the recombinant plasmid, the transcript is packaged into the virus, and then the virus is released into a medium (Nicolas and Rubinstein "Retroviral vectors," In: *Vectors: A survey of molecular cloning vectors and their uses*, Rodriguez and Denhardt (eds.), Stoneham: Butterworth, 494-513 (1988)). The medium containing the recombinant retroviruses is collected, concentrated, and then used as a gene transfer system.

Gene transfer using second-generation retroviral vectors has been reported. As disclosed by Kasahara et al. *Science,* 266:1373-1376 (1994), variants of moloney murine leukemia viruses (MMLVs) were constructed, and an erythropoietin (EPO) sequence was inserted into an envelope region of the variants, thereby producing chimeric proteins having novel binding characteristics. The gene transfer system of the present invention may also be constructed according to construction strategies for the second-generation retroviral vectors as described above.

iii. AAV Vectors

AAVs may be used as gene transfer systems of the present invention since they are capable of infecting non-dividing cells and various types of cells. Detailed descriptions on the construction and use of AAV vectors are fully disclosed in U.S. Pat. Nos. 5,139,941 and 4,797,368.

Typically, AAVs are constructed by simultaneously transforming a plasmid containing a desired gene sequence located between two AAV terminal repeats (McLaughlin et al., *J. Virol.*, 62:1963-1973 (1988); and Samulski et al., *J. Virol.*, 63:3822-3828 (1989)) and an expression plasmid containing a wild-type AAV coding sequence without terminal repeats (McCarty et al., *J. Virol.*, 65:2936-2945 (1991)).

iv. Other Viral Vectors

Other viral vectors may also be used in the present invention. For example, vectors derived from vaccinia viruses (Puhlmann M. et al., *Human Gene Therapy* 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., *Gene,* 68:1-10 (1988)), lentiviruses (Wang G. et al., *J. Clin. Invest.* 104(11):R55-62 (1999)) or herpes simplex viruses (Chamber R., et al., *Proc. Natl. Acad. Sci USA* 92:1411-1415 (1995)) may be used in the present invention.

The complex of the present invention may include a therapeutic gene.

The term "therapeutic gene" used herein refers to a gene capable of encoding a polypeptide (polynucleotide sequence), which may exhibit a therapeutic or preventive effect in intracellular expression. The therapeutic gene is not limited to a type of a target disease as long as it may be included in the complex of the present invention and may include a separate promoter for gene expression. Also, the present invention may include one or two or more of the therapeutic genes.

The term "treatment" used herein refers to all behaviors for beneficially changing clinical events such as suppressing a disease or illness, alleviating or reducing symptoms thereof by administering the polymer-virus complex or composition according to the present invention and also includes "prevention" which means inhibiting symptoms of a disease or delaying the occurrence of a disease.

A form of the therapeutic gene contained in the complex is not limited. For example, the therapeutic gene may be a virus having a therapeutic effect by itself or modified to have a therapeutic effect, or may be bound to or carried by the complex or virus of the present invention, but the present invention is not limited thereto. In one embodiment, the therapeutic gene may be a cancer-treating gene exhibiting a therapeutic effect in expression in cancer cells, and specifically, a drug-sensitizing gene, a tumor suppressor gene, an antigenic gene, a cytokine gene, a cytotoxic gene, a cytostatic gene, a pro-apoptotic gene and an anti-angiogenic gene, but the present invention is not limited thereto.

According to another aspect of the present invention, the present invention provides a pharmaceutical composition including (a) a therapeutically effective amount of the above-described polymer-virus complex of the present invention; and (b) a pharmaceutically acceptable carrier.

The pharmaceutical composition may further include a therapeutic gene.

Since the pharmaceutical composition of the present invention uses the above-described polymer-virus complex and/or therapeutic gene as an active ingredient, to avoid excessive complexity of the specification, repeated descriptions of overlapped content will be omitted.

The pharmaceutical composition including a therapeutically effective amount of the polymer-virus complex of the present invention may be applied regardless of a type of a disease. Specifically, the pharmaceutical composition including the complex of the present invention may be applied to various diseases according to various pharmaceutically active ingredients additionally included in the composition and may be applied for various uses regardless of a disease type. The pharmaceutically active ingredient may be included in the composition together with the complex of the present invention regardless of a disease type, or may be included in the composition by being included in the form the complex of the present invention, and for example, the pharmaceutically active ingredient may be a therapeutic gene. Accordingly, the present invention includes all types of pharmaceutical compositions including the polymer-virus complex of the present invention at a therapeutically effective amount regardless of a disease type.

As described above, the pharmaceutical composition of the present invention is not limited to a disease type and preferably is useful for anticancer treatment. In this respect, the pharmaceutical composition may be a pharmaceutical composition for treating cancer.

In one exemplary embodiment of the present invention, as a result of validating an oncolytic antitumor activity using a polymer/virus complex in which a virus including a therapeutic gene is coated with the polymer of the present invention, the polymer/virus complex had a higher oncolytic antitumor activity than an uncoated virus, and expression of the therapeutic gene in cells and increased expression thereof were experimentally confirmed.

When a gene exhibiting a cancer cell killing effect is inserted into the polymer-virus complex included in the composition of the present invention, the complex exhibits a killing effect with respect to various cancer cells, the pharmaceutical composition of the present invention may be used in treatment of skin, gastrointestinal, urinary, reproductive organ, respiratory organ, circulatory system, brain or nervous cancer. The pharmaceutical composition is specifically used in treatment of lung cancer, non-small cell lung cancer, colon cancer, bone cancer, pancreatic cancer, skin cancer, head and neck cancer, ovarian cancer, uterine cancer, rectal cancer, stomach cancer, anal cancer, breast cancer, carcinoma of the fallopian tube, endometrial cancer, uterine cervical cancer, vaginal cancer, vulvar cancer, Hodgkin's disease, esophageal cancer, small bowel neoplasm, endocrine carcinoma, thyroid cancer, parathyroid carcinoma, adrenal cancer, soft tissue sarcoma, urethral tumor, penile carcinoma, prostate cancer, chronic or acute leukemia, lymphocyte lymphoma, bladder cancer, kidney or ureter cancer, renal cell carcinoma, renal pelvic carcinoma, central nervous system (CNS) tumor, primary CNS lymphoma, spinal cord tumor, liver cancer, bronchial cancer, nasopharyngeal cancer, brain stem glioma or pituitary adenoma.

The term "therapeutically effective amount" used herein means an amount sufficient for achieving a pharmacological effect.

A pharmaceutically acceptable carrier included in the composition of the present invention is conventionally used in preparation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but the present invention is not limited thereto. The pharmaceutical composition of the present invention may further include a lubricant, a wetting agent, a sweetening agent, a flavoring agent, an emulsifier, a suspension, a preservative, etc. in addition to the above components.

In still another embodiment of the present invention, the present invention provides a method of treating a subject, including administering the polymer-virus complex or pharmaceutical composition to a subject required to be treated at a pharmaceutically effective amount.

The pharmaceutical composition of the present invention may be administered parenterally, for example, intravenously, intraperitoneally, intramuscularly, subcutaneously, or topically. The pharmaceutical composition may be administered intraperitoneally to treat ovarian cancer, and may be administered into a portal vein to treat liver cancer. The pharmaceutical composition may be directly injected into a tumor mass for breast cancer, and may be directly injected through an enema to treat colorectal cancer.

The term "pharmaceutically effective amount" used herein refers to an amount sufficient to treat the disease at a reasonable benefit/risk ratio applicable for medical treatment. A suitable dose of the pharmaceutical composition of the present invention may be varied by causes such as a preparation method, an administration method, patient's age, weight and sex, severity of a disease symptom, diet, administration time, an administration route, an excretion rate, and response sensitivity, and an effective dose for desired treatment may be easily determined and prescribed by an ordinary skilled doctor. Generally, the pharmaceutical composition of the present invention includes the polymer-virus complex at $1 \times 10^{-1} \times 10^{15}$ pfu/ml, and is conventionally injected at $1 \times 10^{10}$ pfu every other day for two weeks.

The term "subject" used herein includes animals such as horses, sheep, pigs, goats, camels, antelopes and dogs, or humans, which have a disease whose symptom can be alleviated by administration of the therapeutic composition according to the present invention. As the pharmaceutical composition of the present invention is administered to the subject, a disease may be effectively prevented and treated. The treating method according to the present invention may be a method of treating an animal except a human, but the present invention is not limited thereto. That is, if a human has a disease whose symptom can be alleviated by administering the composition according to the present invention, the composition of the present invention may also be used enough to treat a human disease.

The pharmaceutical composition of the present invention may be prepared by unit-dose packaging or multi-dose packaging after being formulated using a pharmaceutically acceptable carrier and/or excipient according to a method that can be easily implemented by those or ordinary skill in the art. Here, a dosage form may be a solution in an oil or aqueous medium, a suspension or an emulsion, an extract, a powder, a granule, a tablet or a capsule, and the pharmaceutical composition of the present invention may further include a dispersant or a stabilizer.

The pharmaceutical composition of the present invention may be used independently or in combination with another conventional chemotherapy or radiation therapy, and such combination therapy may be more effective in cancer treatment. Chemical therapeutics that can be used together with the composition of the present invention include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. Radiation therapies that can be used together with the composition of the present invention include X-ray radiation and γ-ray radiation.

The present invention provides a bioreducible polymer such as PPSA or PSPA polymer, a polymer-virus complex including the same, and a pharmaceutical composition for treating cancer including the polymer-complex. The complex of the present invention exhibits higher transduction efficiency and a higher therapeutic effect than a conventional polymer-virus complex and therefore can be useful as a pharmaceutical therapeutic agent.

DESCRIPTION OF DRAWINGS

FIGS. 1A, 1B and 1C are $^1$H NMR spectra of samples analyzed by D20: (A) mPEG-PEI; (B) mPEG-PEI-g-Arg; and (C) PPSA.

FIG. 2 is an MALDI-TOF spectrum of PPSA.

FIGS. 3A and 3B show the cytotoxicity of PPSA in A549 and MCF7 cells, assessed by an MIT assay.

FIGS. 4A, 4B, 4C, 4D, 4E and 4F show the cytotoxicity in A549, MCF7 and CT-26 cells according to treating concentrations and time of PEI 25 k, PPSA and PSPA polymers, assessed by an MT assay.

FIGS. 5A, 5B and 5C show characteristics of an Ad/PPSA nanocomplex: (A) The result of gel retardation assay of Ad/PPSA, (B) Average size distribution of naked Ad or Ad/PPSA at various molar ratios, (C) Zeta-potential value of naked Ad or Ad/PPSA at various molar ratios.

FIGS. 6A, 6B and 6C are graphs showing characteristics of the Ad/PPSA complex: (A) Average particle size according to time, (B) Zeta potential according to time, (C) Average size distribution of naked Ad or Ad/PPSA before and after treatment with DTT (5 mM).

FIGS. 7A, 7B and 7C are graphs showing characteristics of the Ad/PSPA nanocomplex: (A) Result of gel retardation assay for the Ad/PPSA complex, (B) Average size distribution and zeta potential of the Ad/PAPS complex, (C) Average size distribution of naked Ad, Ad/PAP and Ad/PAPS before and after treatment with DTT.

FIGS. 8A and 8B are analysis results of transduction efficiency of naked Ad, Ad/25K PEI, Ad/ABP or Ad/PPSA in A549 and MCF7 cells: (A) Fluorescence microscopy images of transduced cells, (B) Transduction efficiency on respective A549 and MCF7 cells, measured by flow cytometry.

FIGS. 9A and 9B are results of a competition assay of naked Ad, Ad/ABP and Ad/PPSA: (A) GFP fluorescence microscopy images and (B) GFP expression levels measured by flow cytometry.

FIGS. 10A, 10B, 10C and 10D show cellular uptake efficiency of naked Ad, Ad/PPS and Ad/PPSA, which are labeled with FITC, observed by confocal microscopy (A, C) and analyzed by FACS (B, D).

FIGS. 11A, 11B and 11C show GFP expression levels of viruses and the virus/polymer complex in respective A549 (FIG. 11A), MCF7 (FIG. 11B) and CT-26 (FIG. 11C) cells.

FIGS. 12A, 12B and 12C are graphs showing GFP expression levels of Ad/PSPA complex, Ad/PPSA complex, and Ad/PEI complex groups in respective A549 (FIG. 12A), MCF7 (FIG. 12B) and CT-26 (FIG. 12C) cells.

FIGS. 13A and 13B are graphs showing a tumor killing effect of DWP418, DWP418/ABP or DWP418/PPSA in A549 (A) and MCF7 (B).

FIGS. 14A, 14B and 14C are graphs showing a tumor killing effect of a virus/polymer complex in A549 (A), MCF7 (B) and CT-26 (C).

FIGS. 15A and 15B show gene expression and increased effects of a virus/polymer complex in cells.

FIGS. 16A and 16B are (A) a graph showing anticancer efficacy of DWP418, DWP418/ABP or DWP418/PPSA in nude mice onto which MCF7 tumors are xenografted, and (B) microscopy images of tumor sections from each group strained with H&E, E1A, PCNA or TUNEL.

FIGS. 17A, 17B and 17C show innate and adaptive immune responses against Ads: (A) Assessment of innate immune response against naked DWP418, DWP418/ABP or DWP418/PPSA by analyzing IL-6 levels in serum by ELISA, and (B, C) Adaptive immune responses against naked Ad and Ad/PPSA by observing a GFP expression level after naked Ad (dE1/GFP) or an Ad/PPSA complex is reacted with serum with or without Ad-specific neutralizing antibody.

FIGS. 18A and 18B show the hepatotoxicity of DWP418, DWP418/ABP and DWP418/PPSA, assessed by measuring ALT (A) and AST (B) levels in serum.

EXAMPLES

Hereinafter, the present invention will be described in further detail with respect to examples. These examples are only provided to more fully describe the present invention, and it is obvious to those of ordinary skill in the art that the scope of the present invention is not limited to these examples, according to the gist of the present invention.

Examples

Test Materials and Method

1. Test Materials

Methoxyl PEG succinimidyl carbonate NHS was purchased from Nanocs (USA). Arginine, N,N-diisopropylethylamine (DIPEA), trifluoroacetic acid (TFA), triisopropyl silane (TIPS), polyethylenimine (1.8 kDa, 50 wt %), branched polyethylenimine (25 kDa), N-hydroxysuccinimide, 2-imidothiolane hydrochloride (Traut's reagent), DL-dithiothreitol, dimethylsulfoxide (DMSO), 2-imidothiolane, 1-Ethyl-3-(3-dimethylaminopropyl) carbodiimide hydrochloride (EDC) and dimethylformaldehyde (DMF) were purchased from Sigma (St Louis, USA).

2-(1-H-Benzotriazole-1-yl)-1,1,3,3-tetramethyluronium hexafluorophosphate (HBTU) was purchased from Novabiochem (San Diego, Calif.). Fmoc-L-Arg(Pbf)-OH was purchased from Anaspec, Inc. (San Jose, Calif.). Ellman's reagent was purchased from Thermo scientific (Rockford, Ill.). Deuterium oxide was purchased from Cambridge Isotope Laboratories, Inc. (Andover, Mass.).

2. Synthesis of mPEG-PEI-g-Arg-S-S-Arg-g-PEI-mPEG (PPSA)

(1) Synthesis of Methoxy Poly(Ethylene Glycol)-Polyethylenimine (mPEG-PEI)

PEG-PEI was synthesized as described in the reference (33). Polyethyleneimide was dissolved in 3.0 ml of PBS (pH 7.4). Subsequently, one molar equivalent of methoxy PEF succinimidyl carbonate NHS (mPEG-NHS, 2.0 kDa) was added. The reaction product was stirred at room temperature overnight. The product was dialyzed against double distilled water at room temperature for 2 hours using a Slide-A-Lyzer dialysis cassette (2.0 kDa MWCO, Pierce, Rockford, Ill., USA) and lyophilized, thereby obtaining a pale white substance (75% yield). The chemical structure of the substance was confirmed by $^1$H NMR observing a D$_2$O-solubilized sample at 300 MHz (Mercury Plus 300 MHz Spectrometer, Varian, Inc. Vernon Hills, Ill., USA). Characteristic PEG (3.6 ppm, —(CH$_2$CH$_2$O)) and PEI (2.0 to 3.0 ppm) peaks were observed.

(2) Synthesis of Arginine-Grafted mPEG-PEI (mPEG-PEI-g-Arg)

As described in the reference (28), arginine was grafted onto mPEG-PEI. The grafting was done by combining 9 equivalents of Fmoc-Arg(Pbf)-OH and HBTU with 12 equivalents of DIPEA in DMF (1.0 ml) at room temperature for 48 hours. The resulting product was precipitated in diethyl ether twice to remove unreacted reagents. To remove the Fmoc moiety from the Fmoc-Arg(Pbf)OH, the precipitant was mixed with an equal volume of 30% piperidine solution in DMF (Sigma, St Louis, Mo., USA) at room temperature for 1 hour. The precipitation process was repeated twice. A reagent solution (TFA:TIPS:H20, 95/2.5/2.5 v/v) was added to the precipitate to remove the Pbf group from the arginine residue. The reaction was performed at room temperature for 30 minutes. The polymer was precipitated with ether. The final product, mPEG-PEI-g-Arg, was dialyzed (2.0 kDa MWCO) against double distilled water overnight and lyophilized, thereby obtaining a white product (60% yield). The chemical structure was confirmed by $^1$H NMR as described above. Characteristic peaks of PEG (3.6 ppm, (CH$_2$CH$_2$O)), PEI (2.0 to 3.0 ppm) and arginine (1.66 ppm (HCCH$_2$CH$_2$CH$_2$NH); 1.86 ppm (HCCH$_2$CH$_2$CH$_2$NH); 3.24 ppm (HCCH$_2$CH$_2$CH$_2$NH); 3.86 ppm (HCCH$_2$CH$_2$CH$_2$NH)) were observed.

(3) Synthesis of mPEG-PEI-g-Arg-S-S-Arg-g-PEI-mPEG (PPSA)

mPEG-PEI-g-Arg was dissolved in PBS (2.0 ml, pH 7.4, 4 mg/ml EDTA). 8 equivalents of 2-imidothiolane hydrochloride (Traut's reagent) per surface amine in mPEG-PEI-g-Arg were added and continuously stirred at room temperature for 3 hours. The product was dialyzed against double distilled water (2.0 kDa MWCO) to remove unreacted reagents and was lyophilized.

The lyophilized mPEG-PEI-Arg-SH was dissolved in 1×PBS, and 500 µl DMSO was added to oxidize the SH group. The reaction product was stirred at room temperature for 48 hours. The product was then dialyzed against double distilled water (2.0 kDa MWCO) again for 24 hours. The final product, mPEG-PEI-g-Arg-S-S-Arg-g-PEI-mPEG (PPSA), was lyophilized, thereby obtaining a white product (80% yields). As described in the reference, the disulfide cross-linking was confirmed by Ellman test (34).

3. Synthesis of PEI-Arg-mPEG-S-S-mPEG-Arg-PEI (PSPA)

(1) Synthesis of Poly(Ethylenimine)-Arginine (PEI-Arg)

Arginine was conjugated to polyethylenimide according to the procedure reported in the literature "Enhanced in-vitro transfection and biocompatibility of L-arginine modified oligo(-alkylaminosiloxanes)-graft-polyethylenimine." The carboxyl group of the amino acid, arginine (350 mg, 2.0 mmol), was activated with a coupling agent, EDC/NHS (EDC, 384 mg, 2.0 mmol and NHS=230 mg 2.0 mmol) in phosphate saline buffer (pH 7.4, 3.0 ml) at 4° C. for 4 hours. Subsequently, polyethylenimine (PEI; 360 mg, 0.2 mmol) was added to the activated arginine, and the reaction was maintained at room temperature for 18 hours. The product was dialyzed (MWCO 1.0 kDa) against double distilled water for a day to remove unreacted compounds and was lyophilized. The chemical structure was confirmed by $^1$H NMR (300 MHz, D2O). A characteristic PEI peak was observed at 2.0 to 3.0 ppm, and characteristic arginine peaks were observed at 1.66 (—HCCH$_2$CH$_2$CH$_2$NH—); 1.86 (—HCCH$_2$CH$_2$CH$_2$NH—); 3.24 (—HCCH$_2$CH$_2$CH$_2$NH—); and 3.86 (—HCCH$_2$CH$_2$CH$_2$NH—).

(2) Synthesis of PEI-Arg-mPEG

Arginine-grafted poly(ethyleneimide) was dissolved in 3.0 ml PBS (pH 7.4). Subsequently, one equivalent of methoxy PEG succineimidylcarbonate NHS-2.0 kDa was added. The reaction mixture was stirred at room temperature overnight. The product was dialyzed against double distilled water at room temperature for 24 hours using a Slide-A-Lyzer dialysis cassette (2.0 kDa MWCO, Pierce, Rockford, Ill., USA) and lyophilized, thereby obtaining PEI-Arg-mPEG.

The chemical structure was confirmed by $^1$H NMR (300 MHz, D$_2$O). The NMR spectrum showed characteristic PEG peak (3.6 ppm, —(CH$_2$CH$_2$O)—), PEI peak (2.0 to 3.0 ppm) and arginine peaks 1.66-(—HCCH$_2$CH$_2$NH—); 1.86 (—HCCH$_2$CH$_2$CH$_2$NH—); 3.24 (—HCCH$_2$CH$_2$CH$_2$NH—); 3.86 (—HCCH$_2$CH$_2$CH$_2$NH—).

(3) Synthesis of PEI-Arg-mPEG-S-S-mPEG-Arg-PEI (PSPA)

PEI-Arg-mPEG was dissolved in IX PBS (2.0 mL, pH=7.4, 4 mg/mL EDTA). 8 equivalents or higher of 2-imidothiolane hydrochloride (Traut's reagent) was added per surface imine of PEI-Arg-mPEG and continuously stirred at room temperature for 3 hours. The product was dialyzed against double distilled water using an Slide-A-dialysis cassette (2.0 kDa MWCO) to remove unreacted reagents, and the product, PEI-Arg-mPEG-SH, was lyophilized. In addition, the lyophilized mPEG-PEI-Arg-SH polymer was redissolved in 1×PBS, and 500 µl DMSO was added to oxidize the SH group. The reaction mixture was stirred at room temperature for 48 hours, and then the product was dialyzed against double distilled water for 24 hours using a Slide-A-dialysis cassette (2.0 kDa MWCO) again. The product was lyophilized to obtain PEI-Arg-mPEG-S-S-mPEG-Arg-PEI (PSPA).

4. Cell Lines and Cell Culture

The following cell lines were purchased from the American Type Culture Collection (ATCC, Manassas, Va.): HEK293, a human embryonic kidney cell line expressing Ad E1 replication protein; A549, a non-small cell lung cancer cell line; MCF7, a breast cancer cell line; and CT-26, a colorectal cancer cell line. All cell lines were cultured in DMEM (Gibco BRL, Grand Island, N.Y.) containing 10% FBS (Gibco BRL) and penicillin/streptomycin (Gibco BRL) at 37° C. in a humidified 5% CO$_2$ atmosphere.

5. Ad Preparation

Replication-incompetent Ad (dEl/GFP) expressing green fluorescent protein (GFP) under the control of a CMV promoter in an E1 region and oncolytic Ad (DWP418 or RdB/IL-12/decorin; oAd) were used basically using the methods described in the previous research that had been conducted by the inventor (35-38). All Ads were propagated in HEK293 cells and then purified by CsCl (Sigma, St Louis, Mich.) density-gradient centrifugation. A viral particle (VP) number was calculated from OD$_{260}$ measurement, for which an absorbance of 1 was equivalent to $10^{12}$ VP/ml.

Infectious titers (PFU/mL) were determined using a limiting dilution assay on HEK293 cells. The viral particle/PFU ratios for dEl/GFP and DWP418 were 29:1 and 81:1, respectively. The MOI was calculated from the infectious titers.

6. Cytotoxicity Analysis

Cytotoxicity of the polymers of the present invention and various cationic polymers was analyzed. Specifically, quantitative cell viability was analyzed on 25 kDa branched polyethylenimine (25 kDa PEI), the previous Ad-binding polymer (ABP), PSPA (PAPS) polymer and PPSA polymer by a method of measuring conversion of MTT to formazan over time (39, 40).

A549 and MCF7 cells were cultured to 50% confluence in 96-well plates, and then each was treated with each of the 25 k PEI polymer, the ABP polymer and the PPSA polymer at concentrations of 0.5 µg/ml, 1 µg/ml, 5 µg/ml and 10 µg/ml. Three days after the polymer treatment (72-hour treatment), 100 µl of MTT (2 mg/ml) was added to each well, and reacted at 37° C. for 4 hours. The supernatant was discarded, and the precipitate was dissolved in 100 μl DMSO. Plates were analyzed on a microplate reader (Bio-Rad, Hercules, Calif.) at 540 nm.

Also, the cytotoxicity of the polymers was measured by the same method as above, except that A549, MCF7 and CT-26 were treated with 0.1 μg/ml, 0.5 μg/ml, 1 μg/ml, 5 μg/ml and 10 μg/ml of each of the 25 k PEI polymer, the PPSA polymer and the PSPA polymer for 24 hours and 72 hours.

7. Preparation of Ad/PPSA Complex

To construct the Ad/PPSA complex, Ad particles ($2 \times 10^{10}$ VP/PBS, pH 7.4) were mixed with various concentrations of the PPSA polymer. As a result, PPSA ratios per Ad particle came to $2 \times 10^4$, $1 \times 10^5$, $4 \times 10^5$ and $1 \times 10^6$. The solution was incubated at room temperature for 30 minutes before use.

8. Preparation of Ad/PSPA Complex

To construct an Ad/PSPA complex, Ad particles ($2 \times 10^{10}$ VP/PBS, pH 7.4) were mixed with various concentrations of the PSPA polymer. As a result, PSPA ratios per Ad particle came to $2 \times 10^3$, $5 \times 10^3$, $1 \times 10^4$, $5 \times 10^4$, $1 \times 10^5$, $5 \times 10^5$, $1 \times 10^6$. The solution was incubated at room temperature for 30 minutes before use.

9. Measurement of Particle Size and Surface Change

Average particle sizes and surface changes of naked Ad and Ad/PPSA were determined by dynamic laser scattering (DLS) at 488 nm and zeta particle analysis (90° fixed angle scattering) at 633 nm, respectively, at room temperature using Zetasizer 3000HS (Malvern Instrument Inc., Worcestershire, UK) with a HeNe laser.

Also, average particle sizes, surface changes such as zeta potential and changes in average particle size according to DTT treatment were assessed on the Ad/PAPS complex by the same method as described above.

In the specification, the sizes and variations are average values of five independent runs.

10. Gel Retardation

Gel retardation was performed to examine the encapsulation profiles of the Ad/PSPA and the Ad/PPSA complex. After the construction of the Ad/PPSA complex, a virus lysis buffer (0.1% SDS, 1 mM Tris-HCl (pH7.4), 0.1 mM EDTA) was added to the Ad/PPSA complex and reacted at 56° C. for 30 minutes. The Ad/PPSA complex sample was loaded on a 1% (w/v) agarose gel in 1×TAE buffer (10 mM Tris-HCl, 1% (v/v) acetic acid, 1 mM EDTA (w/EtBr)). Electrophoresis was performed at 100 V for 30 minutes in the same buffer. The locations of DNA bands were visualized using a Chemi-Doc gel documentation system (Syngene, Cambridge, UK). Gel retardation was also performed on the analyzed Ad/PAPS complex by the same method described above.

11. Analysis of Transduction Efficiency

Each type of cancer cells (A549, MCF7 and CT-26) were seeded into a 24-well plate and cultured to 60% confluence one day before transduction assay. The cells were treated with naked Ad (dE1/GFP) or Ad (dE1/GFP)/polymer complex (Ad/25 KDa PEI, Ad/ABP, Ad/PSPA or Ad/PPSA).

The transduction efficiency was analyzed by assessing GFP expression levels of the PPSA:Ad complex, 25 k PEI complex and ABP complex having the polymervirus molar ratios of $2 \times 10^4$, $1 \times 10^5$, $4 \times 10^5$ and $1 \times 10^6$ in the A549 and MCF7 cell lines.

Also, the transduction efficiency was analyzed in each of A549, MCF7 and CT-26 cell lines using PAPS:Ad complex, PPSA:Ad complex and 25 kDa PEI:Ad complex molar ratios of $1 \times 10^3$, $5 \times 10^3$, $1 \times 10^4$, $5 \times 10^4$, $1 \times 10^5$, $5 \times 10^5$, $1 \times 10^6$. Due to the varying Ad susceptibility of each cell line, different MOI were applied to A549, CT-26 and MCF7.

Transduced cells were further cultured for 48 hours. The cells were imaged using fluorescence microscopy (Olympus IX81; Olympus Optical, Tokyo, Japan), and the GFP expression levels were quantified using FACS analysis BD FAC-Scan analyzer (Becton Dickinson, San Jose, Calif.) and CellQuest software (Becton-Dickinson). Data from 10,000 events were collected, and the mean±standard deviations of three independent experiments were presented.

12. Competition Assay

A549 cells ($5 \times 10^4$ cells/well) were seeded into a 24-well plate. Following 24-hour culture, the cells were pre-treated with PBS or purified Ad fiber knob protein (2 or 10 mg/ml) for 30 minutes. The cells were washed with PBS three times and then treated with 30 MOI of naked Ad or Ad/PPSA complex ($1 \times 10^6$ PPSA:Ad molar ratio) in 5% FBS-supplemented DMEM. The cells were incubated for 2 days, imaged using the fluorescence microscopy (Olympus IX81; Olympus Optical), and analyzed by the BD FACScan analyzer (Beckton-Dickinson) and the CellQuest software (Beckton-Dickinson).

13. Evaluation of Cancer Cell Killing Effect of Oncolytic Ad

To evaluate the cancer cell killing effect of oncolytic Ad, each type of A549 and MCF7 cell lines were seeded into a 96-well plate, and after 24 hours, naked DWP418 and DWP418/ABP, DWP418/PPSA complexes were treated. After 48 hours, medium was removed, 100 μl of MTT (2 mg/ml) was added to each well, and the cells were cultured at 37° C. for 4 hours. Supernatant was discarded, and pellets were dissolved in 100 μl of DMSO. Plates were analyzed on a microplate reader (Bio-Rad, Hercules, Calif.) at 540 nm.

Also, the A549, MCF7 and CT-26 cell lines were seeded in 96-well plates, respectively, and after 24 hours, treated with naked RdB/IL-12/decorin; oAd, oAd/PPSA and oAd/PAPS complexes. After 48 hours, medium was removed, 100 d of MT (2 mg/ml) was added to each well, and the cells were cultured at 37° C. for 4 hours. Supernatant was discarded, and pellets were dissolved in 100 μl of DMSO. Plates were analyzed on a microplate reader (Bio-Rad, Hercules, Calif.) at 540 nm.

14. Western Blotting

To validate production of DCN proteins in cells when CT-26 cell lines were infected by oAd/PAPS complex in which the surface of the virus expressing decorin and IL-12 is coated with PAPS, the CT-26 cells were treated with each of 100, 200 and 500 MOI of naked oAd and oAd/PAPS ($1 \times 10^5$ polymer:virus molar ratio), and after 48 hours, both of the cell culture and the cells were harvested to perform sodium-dodecyl sulfate poly-acrylamide gel electrophoresis (SDS-PAGE). After electrophoresis, proteins in the gel were electrophoretically transferred to a polyvinylidene fluoride (PVDF) membrane and reacted with antibodies specifically recognizing decorin as primary antibodies. After being reacted with horse radish peroxidase (HRP)-binding goat anti-mouse IgG as a secondary antibody, the binding of the proteins on the membrane with the antibodies was detected and protein expression patterns were determined using LAS4000 by enhanced chemiluminescence (ECL; Pierce, Rockford, Ill., USA).

15. ELISA for Detecting Change in IL-12 Expression

Enzyme-linked immunosorbent assay (ELISA) was performed to detect secretion of cytokine to a cell culture when CT-26 cell lines were infected by oAd/PAPS complex in which the surface of a virus expressing decorin and IL-2 is coated with PAPS. One day after the CT-26 cell lines were seeded into a 12-well plate at a density of $5 \times 10^5$ cell/well, the cells were treated with each of 100 and 200 MOI of naked oAd and oAd/PAPS, and after 48 hours, a medium was retrieved from the cells to quantify the IL-12 expression level through ELISA.

16. In Vivo Anticancer Effect and Histological Analysis

MCF7 cells ($5 \times 10^6$) were subcutaneously injected into 6 week-old female nude mice (Orientbio Inc., Gyeonggi-do, Korea). When the tumor volume reached approximately 100 mm³, the mice were injected with PBS, naked Ad, ABP, PPSA, Ad/ABP, or Ad/PPSA ($5 \times 10^{10}$ VP per injection, $1 \times 10^6$ PPSA:Ad molar ratio) into tumors of the mice every other day for 5 days (total three injections). Tumor growth was assessed every two days by caliper measurement and volume calculation as follows: volume (mm³)=0.523×height (mm)×area (mm²). For histological analyses, three days after the final treatment, tumors were harvested, fixed in 10% formalin, and embedded in paraffin. Tumor sections (5 μm thickness) were stained with hematoxylin and eosin (H&E) and examined by light microscopy at 100× magnification.

For immunohistochemical analyses, paraffin-embedded tumor tissues were first deparaffinized by incubation in xylene for 10 minutes and then sequentially incubated with 100%, 900% and 70% ethanol for 5 minutes each.

The tissues were blocked with 3% bovine serum albumin (BSA) at room temperature for 2 hours and stained with Ad E1A-specific antibody (SC-430; Santa Cruz Biotechnology, Santa Cruz, Calif.) or proliferating cell nuclear antigen (PCNA)-specific antibody (Neomarkers, Freemont, Calif.). Sections were counterstained with Mayer's hematoxylin. Apoptosis detection by UNEL analysis was performed using an Apoptag detection kit (Serologicals Corp., Norcross, Ga.) according to the manufacturer's instructions.

17. Assay for Innate Immune Response

To determine the effects of naked DWP418, DWP418/ABP, or DWP418/PPSA complex on the innate immune response, Balb/C mice were systemically injected with the naked DWP418, DWP418/ABP, or DWP418/PPSA complex ($2 \times 10^{10}$ VP per mouse, $1 \times 10^6$ PPSA:Ad molar ratio). Serum samples were collected 6 hours after injection. IL-6 serum levels were quantified using an IL-6 ELISA kit (R&D Systems, Minneapolis, Minn.) according to the manufacturer's instructions.

18. Assay for Adaptive Immune Response

For assessing adaptive immune response against Ad, naked Ad (dE1/GFP) was intravenously injected into Balb/c mice at a single dose of $1 \times 10^{10}$ VP, and 14 days later, Ad was administered again to generate a neutralizing antibody against Ad. 14 days after the second injection, mouse serum immunized with naked Ad (or without naked Ad) was harvested, incubated at 56° C. for 45 minutes to inactivate blood complement, and then stored at 20° C. Naked dE1/GFP (30 MOI) or dE1/GFP coated with PPSA polymer ($1 \times 10^6$ molecules/VP; 30 MOI) was exposed to PBS or serum (with or without Ad-specific neutralizing antibody) at 37° C. for 30 minutes and added to human cancer cells (A549). Two days after incubation, GFP expression levels were analyzed by fluorescence (Olympus BX51) and FAC-Scan flow cytometry (Beckton-Dickinson).

19. In Vivo Toxicity Assessment

To evaluate in vivo potential toxicity, naked DWP418, DWP418/ABP, or DWP418/PPSA ($2 \times 10^{10}$ VP/mouse, $1 \times 10^6$ PPSA:Ad molar ratio) was intravenously injected into Balb/C mice. Three days after injection, serum levels were measured by aspartate aminotransferase (AST) and alanine transaminase (ALT).

20. Statistical Analysis

Data were expressed as mean±standard deviation (SD). Statistical analyses were performed by a two-tailed Student t test (SPSS 13.0 software; SPSS, Chicago, Ill.), and the P value of less than 0.05 was considered statistically significant.

Test Results

1. Synthesis and Characterization of Bioreducible Polymer

High molecular weight branched polyethylenimide (25K PEI) is used as the benchmark for non-viral gene transfer due to high in vitro and in vivo transduction efficacy (42). However, the polymer has significant cytotoxicity and is not biodegradable, and thus clinical application is limited. To solve such a problem, the inventors designed and synthesized a novel cationic polymer which has low cytotoxicity and is biodegradable using PEI with a low molecular weight (1.8 kDa) in the previous research. PEG-complexed PEI was reduced in cytotoxicity, compared to PEI alone (43). PEI cross-linked by bioreducible linkages showed reduced cytotoxicity (44).

Meanwhile, it is known that cell-penetrating peptides containing arginine residues effectively transfer nucleic acids through intracellular translocation (26, 45). Based on such findings, improved biopolymers, PPSA and PSPA, were synthesized.

The main synthetic route of mPEG-PEI-g-Arg-S-S-Arg-PEI-mPEG (PPSA) is summarized in Reaction Scheme 1.

[Reaction Scheme 1]

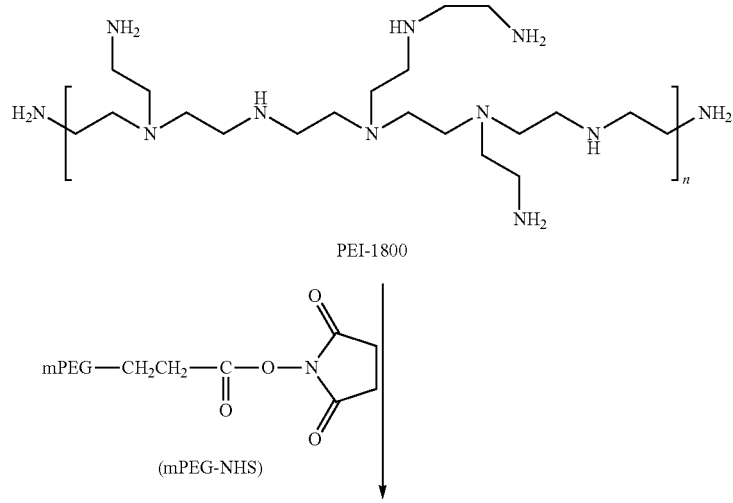

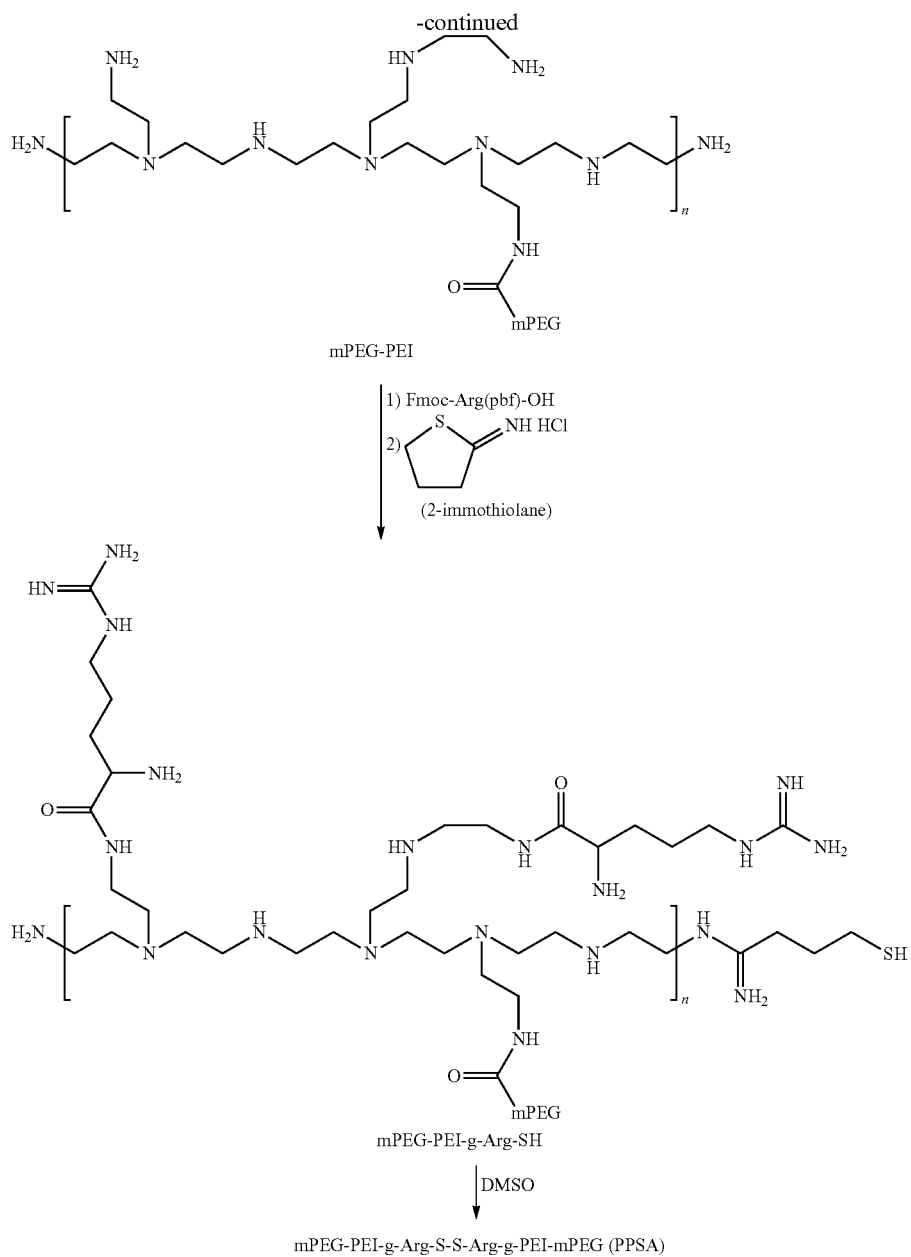

mPEG-PEI-g-Arg-S-S-Arg-g-PEI-mPEG (PPSA)

First, to synthesize mPEG-PEI, PEI 1.8 kDa was reacted with succinimidyl ester methoxy polyethylene glycol (mPEG-NHS) (33). Subsequently, to synthesize mPEG-PEI-g-Arg, arginine was grafted onto the polymer using Fmoc-Arg(Pbf)-OH in the presence of HTBU/DIPEA (28). Afterward, to prepare mPEG-PEI-g-Arg-SH, mPEG-PEI-g-Arg was treated with imidothiolane to link thiol groups to the terminal ends. Finally, a novel bioreducible polymer (mPEG-PEI-g-Arg-S-S-Arg-PEI-mPEG; PPSA) was synthesized by cross-linking the terminal thiol groups using dimethylsulfoxide (DMSO).

The synthesis of PPSA was confirmed by $^1$H NMR (FIG. 1). The occurrence of spectra peaks at 3.64 and 3.36 ppm indicated the presence of methylene protons corresponding to $CH_2CH_2O$ and $OCH_3$ PEG end groups. Three peaks observed at 2.2 to 3.0 ppm correspond to the $CH_2$ NH-methane protons of PEI (FIG. 1A). Such results are consistent with the previous reports (33). Following addition of arginine groups, characteristic arginine peaks appeared at 1.44, 1.70, 3.2 and 3.86 ppm, and were assigned to the methylene and methyne protons of ($HCCH_2CH_2CH_2NH$), ($HCCH_2CH_2CH_2NH$), ($HCCH_2CH_2CH_2NH$) and ($HCCH_2CH_2CH_2NH$), respectively (FIG. 1B). The amount of the grafted arginine was calculated by integrating the area under the PEI methylene peaks ($CH_2CH_2N$) at 2.3 to 3.0 ppm and the arginine methylene peak ($HCCH_2CH_2CH_2NH$) at 1.7 ppm. By the calculations, it was shown that approximately seven arginines were grafted per mPEG-PEI. Also, new characteristic peaks were observed at 1.8 to 2.2 ppm.

These peaks correspond to cross-linker, iminothiolane methylene protons (NHCH(NH$_2$)CH$_2$CH$_2$CH$_2$SS) (FIG. 1C), which showed that (mPEG-PEI-g-Arg-S-S-Arg-g-PEI-mPEG (PPSA) was synthesized. Also, the molecular weight was analyzed by MALDI-TOF-Mass. As a result, it was confirmed that the final polymer molecular weight is approximately 10.6 kDa.

The main synthetic route of PEI-Arg-mPEG-S-S-mPEG-Arg-PEI (PSPA) is summarized in Reaction Scheme 2.

[Reaction Scheme 2]

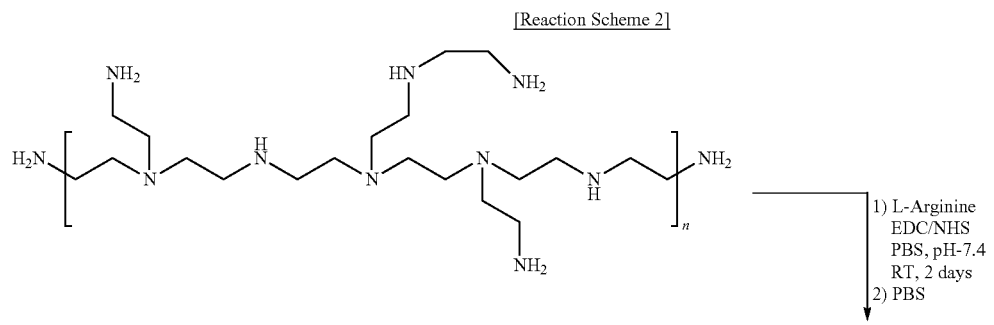

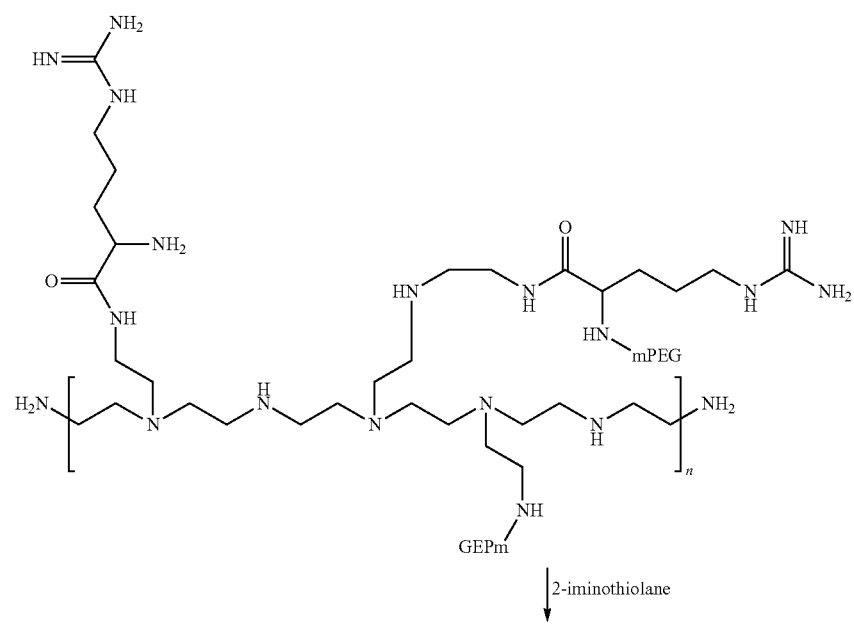

-continued

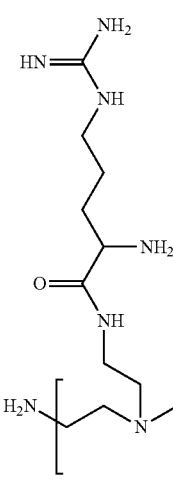
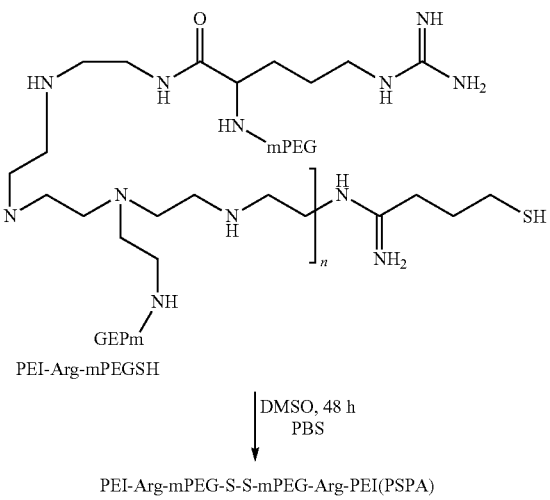

PEI-Arg-mPEGSH

↓ DMSO, 48 h
  PBS

PEI-Arg-mPEG-S-S-mPEG-Arg-PEI(PSPA)

PSPA was synthesized by the following procedures: arginine was added to polyethylenimine (PEI) in PBS in the presence of EDC/NHS as a coupling agent at room temperature for 18 hours, thereby synthesizing PEI-Arg. In the $^1$H NMR spectra for the PEI-Arg, resonance peaks at 1.44, 1.70, 3.2 and 3.86 ppm were assigned to the methyne protons of (—HCCH$_2$CH$_2$CH$_2$NH—); (—HCCH$_2$CH$_2$CH$_2$NH—); (—HCCH$_2$CH$_2$CH$_2$NH—); and (—HCCH$_2$CH$_2$CH$_2$NH—) of arginines grafted with PEI. Also, the amount of the grafted arginines was calculated by integrating the area under the 2.3 to 3.0 ppm PEI methylene peaks (CH$_2$CH$_2$N) and the 1.7 ppm arginine methylene peak (HCCH$_2$CH$_2$CH$_2$NH). By the calculation, it was shown that approximately 5 to 6 arginines per PEI were grafted. To improve biocompatibility and hydrophilic blocks, PEI-Arg was treated with succinimidyl ester methoxy poly(ethylene glycol) (MPEG-NHS) in PBS to create PEI-Arg-mPEG. By $^1$H NMR for determining the chemical structure, new peaks appeared at 3.4 and 3.6 ppm and assigned to ethylene glycol (CH$_2$—CH$_2$—O) and methyl (OCH$_3$) protons in addition to the PEI-Arg peaks, which indicated linkage of PEG. Next, PEI-Arg-mPE was treated with iminothiolane to synthesize PEI-Arg-mPEG-SH, and terminal thiol groups were oxidized in the presence of a mixture of PBS and DMSO at room temperature for 48 hours, resulting in synthesis of a bioreducible polymer, PSPA. The chemical structure of the polymer PSPA was confirmed by $^1$H NMR (300 MHz, D$_2$O). New characteristic peaks appeared at 1.8 to 2.2 ppm and corresponded to iminothiolane methylene protons (—NH—CH(NH$_2$)—CH$_2$—CH$_2$—CH$_2$—S—S—) cross-linked with PEI-Arg-mPEG, which showed synthesis of the PEI-Arg-mPEGS-S-mPEG-Arg-PEI (PSPA).

2. Cytotoxicity Assays for PPSA and PSPA Polymers

To evaluate the potential cytotoxicity, MTT assays were performed on A549 and MCF7 cells treated with PPSA, a control (Mock), PPSA, 25K PEI or ABP. The cells were treated with each of the polymers at various concentrations of 0.5, 1, 5, and 10 μg/ml, incubated for 72 hours to analyze cell viability, and presented as relative values with respect to the control.

As shown in FIGS. 3A and 3B, the 25K PEI decreased cell viability in all concentration ranges tested. The ABP or PPSA did not show cytotoxic effects up to 10 μg/ml. When 10 μg/ml of the 25K PEI, ABP or PPSA was treated, the cell viability of the A549 cells was approximately 46%, 92% or 97%, respectively. At the same dosage of the 25K PEI, ABP or PPSA, the MCF7 cells showed cell viability of approximately 36%, 94% or 97%, respectively. These results are consistent with the previous reports demonstrating that ABP does not have obvious toxicity to mammal cells (32). Meanwhile, more importantly, PPSA does not show cytotoxicity, either, which seems to be because of the low molecular weight of PEI (1.8 kDa) and PEG conjugation (46).

(2) Cytotoxicity Assays for Polymer According to Time
(1) Cytotoxicity Assay for PPSA To evaluate the potential cytotoxicity, MTT assays were performed on A549 and MCF7 cells treated with PPSA, a control (Mock), PPSA, 25K PEI or ABP. The cells were treated with each of the polymers at various concentrations of 0.5, 1, 5, and 10 μg/ml, incubated for 72 hours to analyze cell viability, and presented as relative values with respect to the control.

As shown in FIGS. 4A, 4B, 4C, 4D, 4E and 4F, when the A549 cell line was treated with 10 μg/ml of the PAPS polymer for 24 hours, the cell viability was 83%. In contrast, when the A549 cell line was treated with 10 μg/ml of PEI widely used for nucleic acid transfer for 24 hours, the cell viability was 15% (FIG. 4A). Also, when the same amount of the PAPS, PPSA, or PEI polymer is added for 72 hours, the cell viability was 75%, 78% or 21%. These results showed that the PAPS polymer has similar cell viability, compared to the cytotoxicity of the PPSA and has a remarkably lower toxicity than PEI. It is estimated that the biodegradable PAPS is able to be reduced into a lower molecular weight, and thus has a lower cytotoxicity than the non-biodegradable PEI. Accordingly, the PAPS has remarkably increased biocompatibility than 25 kDa PEI. Similar results according to the same concentrations and treating time were also obtained from the other cell lines such as MCF7 and CT-26.

3. Characterization of Nanocomplex (1) Characterization of Ad/PPSA Nanocomplex

To evaluate the capability of PPSA to form a complex with Ad, comparative agarose gel retardation electrophoresis assays were performed on the polymer at various molar ratios of 0 (naked Ad), $2\times10^4$, $1\times10^5$, $4\times10^5$, and $1\times10^6$ per Ad particles.

As shown in FIGS. 5A, 5B and 5C, Ad migration was gradually increased with increased PPSA:Ad molar ratios. The Ad migration was completely retarded at the molar ratio of $1\times10^6$, which indicated that an Ad surface was saturated with the PPSA polymer (FIG. 5A).

It is important for a gene transfer vector to have a proper size (<200 nm) for efficient cellular uptake through a non-specific clathrin-dependent process (47, 48). Also, the complex is required to be overall positively charged for being more effectively attached to a negatively-charged cell membrane. To evaluate the biophysical characteristic of Ad/PPSA nanoparticles, the hydrated size and surface charge were measured by DLS and zeta potential analyzer. The average naked Ad particle size in a solution was 110.8 nm in diameter and increased up to 200 nm ($1\times10^6$ molar ratio), proportional to an increased molar ratio of PPSA:Ad (FIG. 5B).

In agreement with the DLS data, surface charge was also increased from 19.7±1.2 mV (naked Ad) to 19.6±0.9 mV ($1\times10^6$ molar ratio), proportional to the increased PPSA:Ad molar ratio (FIG. 5C). These results show that, through electrostatic interaction, the Ad surface was successfully coated with PPSA that shielded negative charge and thus had a net positive charge at a molar ratio of $1\times10^5$ or higher.

The colloidal stability of Ad/PPSA nanoparticles in PBS buffer was measured at room temperature for up to 72 hours by a method of measuring the average size and surface charge of the nanoparticle of the Ad/PPSA complexes with molar ratios of the polymer per Ad particle of $4\times10^5$ and $1\times10^6$. Also, the reducibility of the PPSA and non-reducible mPEG-PEI-g-Arg (PPA) was examined by treatment with dithiothreitol (DTT) as a reducing agent. The particle sizes of the naked Ad, Ad/PPSA and Ad/PPA complexes, each of which was either treated or not treated with DTT, were measured by a DLS analyzer.

As shown in FIGS. 6A and 6B, the average size and surface charge of the Ad/PPSA nanoparticle were not significantly changed for 72 hours, which implies that PPSA cationic polymer-coated Ad has excellent colloidal stability.

Also, as shown in FIG. 6C, the size of the naked Ad or Ad/PPA complex was not changed by DTT treatment. However, the average particle size of the PPSA-coated Ad complex was significantly reduced after the DTT treatment and approximated the size of the naked Ad. This result clearly confirmed that PPSA is biodegradable in a reducible microenvironment.

Taken together, the test results show that the Ad/PPSA complex was successfully constructed to form a particle with a diameter of less than 200 nm (FIG. 6A), created a positively charged surface (FIG. 6B), and thus was able to be effectively transduced into cells.

(2) Characterization of Ad/PSPA Nanocomplex

Comparative agarose gel retardation electrophoresis assays were performed to analyze the interaction between the Ad/PAPS complex and Ad according to various concentration ratios. The test was performed on the complex having various molar ratios of the polymer per Ad particle of $1\times10^3$, $5\times10^3$, $1\times10^4$, $1\times10^5$, $5\times10^5$ and $1\times10^6$.

As shown in FIG. 7A, Ad migration through the gel was retarded with an increased polymer ratio, which indicates that the Ad surface charge was converted to be positive. When the polymer and Ad ratios exceed the neutralization point, the surface charge of the complex was converted to be positive, thereby interrupting migration. When the molar ratio was $1\times10^5$, Ad was not migrated, which indicates that the Ad surface was saturated by PAPS at the above concentration. Also, from such a result, the Ad band was not observed, indicating that the PAPS polymer effectively forms a complex with Ad.

To evaluate the biophysical characteristic of the Ad/PAPS nanoparticle, the hydrated size and surface charge were measured by DLS and zeta potential analyzer. The average naked Ad particle size in a solution was 124.8 nm in diameter, was maintained below approximately 200 nm for PSPA:Ad molar ratio up to $1\times10^5$, and, at a higher molar ratio, increased up to 935.6 nm ($1\times10^6$ molar ratio), proportional to the molar ratio (FIG. 7B).

In agreement with the DLS data, the surface charge was also increased from −21.8±0.75 mV (naked Ad) to 19.7±4.9 mV ($1\times10^6$ molar ratio), proportional to the increased PPSA:Ad molar ratios (FIG. 7B). These results show that the Ad surface was successfully coated with PAPS through electrostatic interaction and thus finally had a positively charged surface.

Also, the reducibility of the PAPS and non-reducible PEI-Arg-mPEG (PAP) was examined by treatment with dithreitol (DTT) as a reducing agent. The particle sizes of the naked Ad, Ad/PAPS and Ad/PAP complexes, each of which was either treated or not treated with DTT, were measured by a DLS analyzer. As a result, the size of the naked Ad or Ad/PAP complex was not changed by DTT treatment (FIG. 7C). However, the average particle size of the PAPS-coated Ad complex was significantly reduced after the DTT treatment and approximated the size of the naked Ad. Such a result proves that the PAPS is biodegradable under a reducible microenvironment.

Taken together, the test results show that the Ad/PAPS complex was successfully constructed to form a particle having a diameter of less than 200 nm for the molar ratio of polymer:Ad of $1\times10^5$, created a positively charged surface, and thus was effectively transduced into cells.

4. Enhanced Transduction Efficiency of Ad/PPSA Complex

Ad-mediated gene transfer is dependent on the CAR expression level on a target cell membrane. However, malignant tumors often down-regulate CAR expression, resulting in poor Ad tumor infectivity (49, 50). Therefore, it is necessary to develop a CAR pathway-independent delivery method in order to ensure the delivery of an effective gene therapeutic agent.

To evaluate the ability of Ad/PPSA to bypass CAR-mediated transfer, Ad/PPSA was transduced into CAR(+) A549 cells and CAR(−) MCF7 cells, and 25K PEI and Ad/ABP complex were used as controls. The inventors have confirmed in a previous research that Ad/ABP complex enters into cells through a CAR-independent cell transfer pathway, has tolerance to Ad infection, and promotes the gene transfer even in cells with low CAR expression (32).

As shown in FIGS. 8A and 8B, the transduction efficiency of Ad/PPSA was considerably increased in all of the A549 and MCF7 cells, compared to the naked Ad. This shows that Ad/PPSA may be effectively CAR expression-independently transduced into cancer cells. Importantly, the effect of the PPSA complex was shown in CAR(−) MCF7 cells, and the transduction efficiency was increased 107 times ($4\times10^5$ PPSA:Ad molar ratio) and 110 times ($1\times10^6$ PPSA:Ad molar ratio), compared to the naked Ad (P<0.001). More importantly, at the $4\times10^5$ polymer:Ad molar ratio, GFP expression in the A549 and MCF7 cells treated with Ad/ABP was increased two-fold higher than that in the Ad/PPSA-treated cells (P<0.001). This shows the superiority of Ad/PPSA in terms of transduction efficiency. Meanwhile, the GFP expression in the Ad/25K PEI-treated cells was lower than those treated with naked Ad, which may be caused by significant cytotoxicity of 25K PEI.

Also, to further confirm CAR-independent cell introduction of Ad/PPSA, competition assays were performed using Ad5 knob protein binding to CAR.

As shown in FIGS. 9A and 9B, when the A549 cells were pretreated with a knob protein, naked Ad-treated cells had significantly decreased GFP expression in a dose-dependent manner, such as decreasing by 56.1% (2 mg/ml knob protein treatment) and 81.1% (10 mg/ml knob protein treatment). Meanwhile, GFP expression of Ad/ABP was decreased by 27.2% (2 mg/ml knob protein treatment) and 53.8% (10 mg/ml knob protein treatment), and GFP expression of Ad/PPSA was decreased by 12.2% (2 mg/ml knob protein treatment) and 23.3% (10 mg/ml knob protein treatment). These results show that the introduction of Ad/ABP and Ad/PPSA into cells was mainly mediated by CAR-dependent cellular uptake, and had a therapeutic value for treating malignant cancer cells in a clinical aspect.

Cellular uptake efficiency of the Ad/PPSA complex was compared to the naked Ad or mPEG-PEI-S-S-PEI-mPEG (PPS)-coated Ad using FITC fluorescence labeling.

As shown in FIGS. 10A, 10B, 10C and 10D, the Ad/PPS or Ad/PPSA complex was considerably improved in cellular uptake efficiency, compared to the naked Ad (P<0.001). Importantly, the cellular uptake efficiency was significantly increased when the cells were treated with Ad/PPSA, compared to when treated with Ad/PPS (P<0.05). This demonstrates that arginine grafting is able to increase the cellular uptake efficiency.

5. Enhanced Transduction Efficiency of Ad/PSPA

To examine the transduction efficiency of the Ad/PSPA nanocomplex in vitro, GFP expression levels of the Ad/PAPS complex in the MCF7 cell lines, CT-26 cell lines and A549 cell lines having low CAR expression levels were analyzed.

The transduction efficiency of the Ad/PSPA complex was compared to that of the PEI 25 kDa and that of the Ad/PPSA complex which is the other aspect of the present invention. At pH 7.4, 500 MOI (VIRUS OD titer $2\times10^{10}$ VP) of naked Ad, Ad/PSPA nanocomplex, Ad/PPSA nanocomplex and Ad/PEI 25 kDa nanocomplex were transduced into each of the A549, MCF7 and CT-26 cells in $1\times10^3$, $5\times10^3$, $1\times10^4$, $5\times10^4$, $1\times10^5$, $5\times10^5$, and $1\times10^6$ polymer:Ad molar ratios for 48 hours. To visualize the transduction efficiency of each treated vector, green fluorescence images of the cells were analyzed by fluorescence microscopy.

As shown in FIGS. 11B, 11C, 12B and 12C, in the MCF7 and CT-26 cells, GFP expression was not observed when treated with the naked Ad but considerably high GFP expression was observed when treated with the polymer-coated Ad nanocomplex. When treated with the Ad/PPSA complex, the cells exhibited no GFP expression at low concentrations but exhibited dose-dependently increase of GFP expression. When treated with the Ad/PEI 25 kDa complex, the cells exhibited high GFP expression at low concentrations but exhibited decreased GFP expression with increasing capacity. This may be caused by the cytotoxicity of the Ad/PEI 25 kDa complex at high concentration. When treated with the Ad/PAPS complex, the cells exhibited high GFP expression in the $1\times10^5$ polymer:Ad molar ratio and decreased GFP expression with increasing polymer:Ad molar ratio. These results show that the Ad/PAPS complex is able to considerably increase the transduction efficiency even for a polymer Ad molar ratio that is lower than the Ad/PPSA in CAR(−) cells.

Also, as shown in FIGS. 11A and 12A, the transduction efficiency of Ad/PAPS was also considerably increased in the A549 cells, compared to the naked Ad. This shows that the Ad/PAPS is also CAR expression-independently and effectively transduced into cancer cells.

6. Cancer Cell Killing Effect of Virus/Polymer Complex (1) Anticancer Effect of Virus/PPSA Complex Containing Therapeutic Gene To further evaluate the potential therapeutic value of PPSA, oncolytic Ad (DWP418) was formed in a complex with PPSA. DWP418 replication is controlled by a modified TERT promoter and contains relaxin as a therapeutic gene. In the previous research, the inventors have confirmed that DWP418 only replicates in cells with high telomerase activity, which is a common feature of the cancer cells, and relaxin expression increases viral spread throughout tumor tissue by reducing extracellular matrix components (36).

As shown in FIGS. 13A and 13B, naked DWP418 induced cell lysis in CAR(+) A549 cells, but not in CAR(−) MCF7 cells, which means that naked DWP418 is dependent on CAR expression in cell introduction. In contrast, when DWP418 was coated with ABP or PPSA at a $1\times10^6$ polymer:Ad molar ratio, cell killing effect was considerably increased by 34% and 80%, respectively, in MCF7 cells (P<0.001). Likewise, increase in cell killing effect of DWP418/ABP (18% increase) and DWP418/PPSA (40% increase), compared to naked DWP418, in the CAR(+) A549 cells were observed (P<0.001). These results are consistent with enhanced gene transfer efficiency of the nanocomplex, compared to the naked Ad (FIGS. 8A and 8B), and show that the therapeutic effect of the oncolytic Ad may be considerably improved by coating the viral surface with PPSA.

(2) Anticancer Efficacy of Virus/Polymer Complex

A surface of RdB/IL-12/decorin, which is oncolytic Ad (oAd), was coated with either a PPSA polymer or a PAPS polymer to construct a complex. The complex was constructed at a polymer:virus molar ratio of $1\times10^5$.

As shown in FIGS. 14A, 14B and 14C, when CAR(+) A549 cells were treated with 1, 2, and 5 MOI of test groups, respectively, 41%, 61%, and 69% enhanced cell killing effects were exhibited with respective MOI (P<0.001). Also, it was confirmed that, when CAR (−) MCF7 and CT-26 cells were treated with the test groups with volumes of 50, 100 and 200 MOI and 100, 500 and 1000 MOI, respectively, and MCF7 cells were treated with 200 MOI each of the test groups, the cell killing effects of oAd/PAPS and oAd/PPSA were increased by 55% and 29%, respectively, compared to naked oAd. It was confirmed that, when the CT-26 cells were treated with 1000 MOI each of the test groups, the cell killing effects of oAd/PAPS and oAd/PPSA were increased by 63% and 45%, respectively, compared to naked oAd. These results are consistent with the enhanced gene transfer efficiency of the Ad/polymer complex, compared to naked Ad, and showed that the therapeutic effect of the oncolytic Ad was considerably increased by coating the Ad surface with PPSA or PAPS.

7. Confirmation of Increased Gene Expression Efficiency of Ad/PAPS Complex

When CT-26 cell lines were infected by oAd/PAPS complex in which the surface of a virus expressing decorin and IL-12 is coated with PAPS, DCN protein was generated in the cells, and IL-12 cytokine was generated to be secreted to a cell culture. Therefore, in order to confirm increased gene expression efficiency when the complex of the present invention was used, 48 hours after CT-26 cells were treated with 100, 200 or 500 MOI each of naked oAd and oAd/PAPS, both the cell culture and the cells were harvested to perform sodium-dodecyl sulfate poly-acrylamide gel electrophoresis (SDS-PAGE). All of infected tumor cells and medium were harvested and subjected to western blotting using a decorin-detectable antibody.

Subsequently, to confirm IL-12 expression, enzyme-linked immunosorbent assay (ELISA) was performed. 48 hours after the CT-26 cell lines were treated with 100 or 200 MOI of naked oAd and oAd/PAPS, the medium was retrieved from the cells, and IL-12 expression levels were quantified by ELISA.

As shown in FIGS. 15A and 15B, an amount of decorin that is enough to be detected was observed from a 500 MOI of oAd/PAPS-treated cell lysate. However, from the cell lysate treated with naked oAd, decorin expression could not be detected. This is because it is impossible to introduce naked oAd into CAR (−) CT-26 cell lines. Therefore, it was confirmed that oAd/PAPS can also be introduced into CAR (−) CT-26 cell lines, and decorin is generated in the cells.

Also, it was confirmed that IL-12 expression was not observed when the cells were treated with naked oAd used in the test, but an increased IL-12 expression level was observed as MOI increased, when the cells were treated with oAd/PAPS. This means that the generation of a therapeutic substance can be induced through the expression of a therapeutic gene by CAR-independent introduction of the oAd/PAPS complex into the cells.

8. Potential Anticancer Efficacy of Ad/PPSA

To validate the therapeutic anticancer efficacy of DWP418/PPSA, MCF7 tumors xenografted onto nude mice were injected every other day for 5 days (total three injections) with PBS, ABP, PPSA, DWP418, DWP418/ABP or DWP418/PPSA.

As shown in FIGS. 16A and 16B, the injection of DWP418/ABP or DWP418/PPSA into tumors significantly reduced tumor growth, compared to naked DWP418. This result shows that the oncolytic anticancer activity of cationic polymer-coated DWP418 was enhanced (P<0.01). Volumes of the MCF7 xenograft tumors treated with PBS, ABP, PPSA, DWP418, DWP418/ABP, or DWP418/PPSA were 1520±30, 1325±47, 1297±91, 1084±42, 802±42, and 483±79 mm$^3$, respectively, at 18 days after treatment (FIG. 16A). The tumor volumes of the mice treated with DWP418, DWP418/ABP or DWP418/PPSA were reduced by 28.7%, 47.2% and 68.2%, respectively, when compared to the PBS-treated control. 19 days after treatment, DWP418/ABP or DWP418/PPSA treatment resulted in 1.3-fold or 2.24-fold decrease in tumor volumes, compared to naked DWP418 (P<0.01). This result demonstrates excellent anticancer efficacy and an improved therapeutic effect of DWP418/PPSA, compared to DWP418/ABP (P<0.01).

For histological and immunohistochemical analysis, MCF7 tumors treated with PBS, ABP, PPSA, DWP418, DWP418/ABP or DWP418/PPSA were harvested three days after the final injection. Tissue sections were then subjected to staining with Ad E1A-specific antibody, PCNA, and TUNEL as well as standard H & E staining (FIG. 16B). DWP418/PPSA-treated tumor tissue showed extensive necrosis and a larger Ad spread compared to DWP418 or DWP418/ABP-treated tumors. Dark staining of Ad E1A in tumor tissue indicated active replication of oncolytic Ad in infected cancer cells according to PPSA release. Also, proliferating cell nuclear antigen (PCNA) expression in DWP418/PPSA-treated tumor tissue was remarkably reduced compared to naked DWP418 or DWP418/ABP-treated tumor tissue. This result demonstrated that DWP418/PPSA is more effective in inhibiting tumor cell proliferation. Likewise, in the DWP418/PPSA-treated group, TUNEL-positive apoptotic cells are abundant in the region such as E1A-positive cells. Taken together, this result demonstrates that the oncolytic Ad/PPSA complex had enhanced infection ability and increased anticancer efficacy, compared to the naked oncolytic Ad and oncolytic Ad/ABP complex.

9. Innate and Adaptive Immune Response Against Ad

Intravenous Ad injection may activate an innate immune response, which limits the therapeutic efficiency of Ad. To evaluate whether DWP418/PPSA is able to evade the innate immune response, 6 hours after treatment, proinflammatory cytokine IL-6 secretion from mice was measured.

Naked DWP418 induced an increase in IL-6 serum level by 4.87-fold over the base level in Balb/C mice (P<0.01) (FIG. 17A). In remarkable contrast, DWP418/ABP and DWP418/PPSA treatment showed IL-6 serum levels that are almost the same as PBS-treated mice. This result indicates that Ad surface coating with both ABP and PPSA may reduce the innate immune response against Ad.

Also, the potential efficacy of DWP418/PPSA to evade the adaptive immune response against Ad was evaluated. Ad-specific neutralizing antibody-containing serum obtained from a mouse treated with naked Ad (dE1/GFP) reduced the transduction efficiency of naked dE1/GFP by 94.8% (FIGS. 17B and 17C). In contrast, the transduction efficiency of the Ad/PPSA complex was not reduced. This result demonstrates that the PPSA complex can evade pre-existing neutralizing antibodies and further shows that the Ad/PPSA nanocomplex can be used in systemic multidose treatment.

10. In Vivo Hepatotoxicity of Intravenously-Injected Ad/PPSA

To evaluate Ad treatment-related hepatotoxicity, serum ALT and AST levels were measured after intravenous injection of naked DWP418, DWP418/ABP, or DWP418/PPSA.

As shown in FIGS. 18A and 18B, the naked DWP418-treated mice showed a significantly higher transaminase serum level than the PBS-treated control three days after injection (P<0.05). In contrast, no significant increases in ALT and AST levels were observed from the DWP418/PPSA-treated mice. The serum ALT and AST levels were a little decreased in the DWP418/ABP-treated mice, but considerably increased in the PBS-treated mice. These results show that Ad PEGylation induced a decrease in Ad-related hepatotoxicity. The lower hepatotoxicity level in the DWP418/PPSA-treated mice compared to that in the DWP418/ABP-treated mice may be caused by the PEGylated PEI on PPSA.

Above, specific parts of the present invention have been described in detail. It is apparent to those of ordinary skill in the art that such specific descriptions are merely specific embodiments, and the scope of the present invention is not limited thereto. Therefore, the substantial scope of the present invention is to be defined by the accompanying claims and equivalents thereof.

REFERENCES (1) El-Aneed, A. J. Controlled Release 2004, 94, 114.
(2) Meng, F.; Hennink, W. E.; Zhong, Z. Biomaterials 2009, 30, 2180-2198.
(3) Samal, S. K.; Dash, M.; Van Vlierberghe, S.; Kaplan, D. L.; Chiellini, E.; van Blitterswijk, C.; Moroni, L.; Dubruel, P. Chem. Soc. Rev. 2012, 41, 7147-7194.
(4) Park, T. G.; Jeong, J. H.; Kim, S. W. Adv. Drug Delivery Rev. 2006, 58, 467-486.
(5) Coughlan, L.; Alba, R.; Parker, A. L.; Bradshaw, A. C.; McNeish, I. A.; Nicklin, S. A.; Baker, A. H. Viruses 2010, 2, 2290-2355.
(6) Singh, R.; Kostarelos, K. Trend. Biotechnol. 2009, 27, 220-229.
(7) Kasala, D.; Choi, J. W.; Kim, S. W.; Yun, C. O. Expert Opin. Drug Delivery 2014, 11, 379-392.
(8) Roelvink, P. W.; Lizonova, A.; Lee, J. G.; Li, Y.; Bergelson, J. M.; Finberg, R. W.; Brough, D. E.; Kovesdi, I.; Wickham, T. J. J. Virol. 1998, 72, 7909-7915.
(9) Park, J.; Kim, W. J. J. Drug Target. 2012, 20, 6486466.
(10) Neu, M.; Fischer, D.; Kissel, T. J. Gene Med. 2005, 7, 992-1009.
(11) Shen, J.; Zhao, D. J.; Li, W.; Hu, Q. L.; Wang, Q. W.; Xu, F. J.; Tang, G. P. Biomaterials 2013, 34, 45204531.
(12) Coue, G.; Engbersen, J. F. J. Controlled Release 2010, 148, e911.
(13) Esfand, R.; Tomalia, D. A. Drug Discovery Today 2001, 6, 427-436.
(14) Arote, R. B.; Jiang, H. L.; Kim, Y. K.; Cho, M. H.; Choi, Y. J.; Cho, C. S. Expert Opin. Drug Delivery 2011, 8, 1237-1246.
(15) Green, J. J.; Langer, R.; Anderson, D. G. Acc. Chem. Res. 2008, 41, 749-759.
(16) Lin, C.; Blaauboer, C. J.; Timoneda, M. M.; Lok, M. C.; van Steenbergen, M.; Hennink, W. E.; Zhong, Z.; Feijen, J.; Engbersen, J. F. J. Controlled Release 2008, 126, 166-174.
(17) Green, J. J.; Zugates, G. T.; Langer, R.; Anderson, D. G. Method. Mol. Biol. 2009, 480, 53-63.
(18) Fasbender, A.; Zabner, J.; Chillon, M.; Moninger, T. O.; Puga, A. P.; Davidson, B. L.; Welsh, M. J. J. Biol. Chem. 1997, 272, 6479-6489.
(19) Mok, H.; Bae, K. H.; Ahn, C. H.; Park, T. G. Langmuir 2009, 25, 1645-1650.
(20) Mok, H.; Park, J. W.; Park, T. G. Bioconjugate Chem. 2008, 19, 797-801.
(21) Bolhassani, A. Biochim. Biophys. Acta 2011, 1816, 232-246.
(22) Torchilin, V. P. Adv. Drug Delivery Rev. 2008, 60, 548-558.
(23) Levchenko, T. S.; Rammohan, R.; Volodina, N.; Torchilin, V. P. Method. Enzymol. 2003, 372, 33949.
(24) Nam, H. Y.; Kim, J.; Kim, S.; Yockman, J. W.; Kim, S. W.; Bull, D. A. Biomaterials 2011, 32, 5213-5222.
(25) Koren, E.; Torchilin, V. P. Trend. Mol. Med. 2012, 18, 385-393.
(26) Zorko, M.; Langel, U. Adv. Drug Delivery Rev. 2005, 57, 529-545.
(27) Morris, V. B.; Sharma, C. P. J. Colloid Interface Sci. 2010, 348, 360-368.
(28) Kim, T. I.; Ou, M.; Lee, M.; Kim, S. W. Biomaterials 2009, 30, 658-664.
(29) Nam, H. Y.; Hahn, H. J.; Nam, K.; Choi, W. H.; Jeong, Y.; Kim, D. E.; Park, J. S. Int. J. Pharm. 2008, 363, 199-205.
(30) Kim, W. J.; Christensen, L. V.; Jo, S.; Yockman, J. W.; Jeong, J. H.; Kim, Y. H.; Kim, S. W. Mol. Ther. 2006, 14, 343-350.
(31) Won, Y. W.; Yoon, S. M.; Lee, K. M.; Kim, Y. H. Mol. Ther. 2011, 19, 372380.
(32) Kim, P. H.; Kim, T. I.; Yockman, J. W.; Kim, S. W.; Yun, C. O. Biomaterials 2010, 31, 1865-1874.
(33) Zhan, C.; Qian, J.; Feng, L.; Zhong, G.; Zhu, J.; Lu, W. J. Drug Target. 2011, 19, 573581.
(34) Eyer, P.; Worek, F.; Kiderlen, D.; Sinko, G.; Stuglin, A.; Simeon-Rudolf, V.; Reiner, E. Anal. Biochem. 2003, 312, 224-227.
(35) Kim, E.; Kim, J. H.; Shin, H. Y.; Lee, H.; Yang, J. M.; Kim, J.; Sohn, J. H.; Kim, H.; Yun, C. O. Hum. Gene Ther. 2003, 14, 1415-1428.
(36) Kim, J. H.; Lee, Y. S.; Kim, H.; Huang, J. H.; Yoon, A. R.; Yun, C. O. J. Natl. Cancer Inst. 2006, 98, 1482-1493.
(37) Choi, J. W.; Kang, E.; Kwon, O. J.; Yun, T. J.; Park, H. K.; Kim, P. H.; Kim, S. W.; Kim, J. H.; Yun, C. O. Gene Ther. 2013, 20, 880-892.
(38) Kim, P. H.; Kim, J.; Kim, T. I.; Nam, H. Y.; Yockman, J. W.; Kim, M.; Kim, S. W.; Yun, C. O. Biomaterials 2011, 32, 9328-9342.
(39) Kim, P. H.; Sohn, J. H.; Choi, J. W.; Jung, Y.; Kim, S. W.; Haam, S.; Yun, C. O. Biomaterials 2011, 32, 2314-2326.
(40) Kim, J.; Nam, H. Y.; Kim, T. I.; Kim, P. H.; Ryu, J.; Yun, C. O.; Kim, S. W. Biomaterials 2011, 32, 5158-5166.
(41) Yun, C. O.; Cho, E. A.; Song, J. J.; Kang, D. B.; Kim, E.; Sohn, J. H.; Kim, J. H. Hum. Gene Ther. 2003, 14, 1643-1652.
(42) Schaffert, D.; Wagner, E. G Gene Ther. 2008, 15, 11311138.
(43) Kim, W. J.; Yockman, J. W.; Lee, M.; Jeong, J. H.; Kim, Y. H.; Kim, S. W. J. Controlled Release 2005, 106, 224-234.
(44) Han, J.; Zhao, D.; Zhong, Z.; Zhang, Z.; Gong, T.; Sun, X. Nanotechnology 2010, 21, 105-106.
(45) Futaki, S.; Suzuki, T.; Ohashi, W.; Yagami, T.; Tanaka, S.; Ueda, K.; Sugiura, Y. J. Biol. Chem. 2001, 276, 5836-5840.
(46) Huang, F. W.; Wang, H. Y.; Li, C.; Wang, H. F.; Sun, Y. X.; Feng, J.; Zhang, X. Z.; Zhuo, R. X. Acta Biomater. 2010, 6, 4285-4295.
(47) Wiethoff, C. M.; Wodrich, H.; Gerace, L.; Nemerow, G. R. J. Virol. 2005, 79, 992-2000.
(48) Meier, O.; Greber, U. F. J. Gene Med. 2003, 5, 451462.
(49) Matsumoto, K.; Shariat, S. F.; Ayala, G. E.; Rauen, K. A.; Lerner, S. P. Urology 2005, 66, 441-446
(50) Sachs, M. D.; Rauen, K. A.; Ramamurthy, M.; Dodson, J. L.; De Marzo, A. M.; Putzi, M. J.; Schoenberg, M. P.; Rodriguez, R. Urology 2002, 60, 531-536.
(51) Lee, C. H.; Kasala, D.; Na, Y.; Lee, M. S.; Kim, S. W.; Jeong, J. H.; Yun, C. O. Biomaterials 2014, 35, 5505-5516.

What is claimed is:

1. A bioreducible polymer represented by Formula 2,

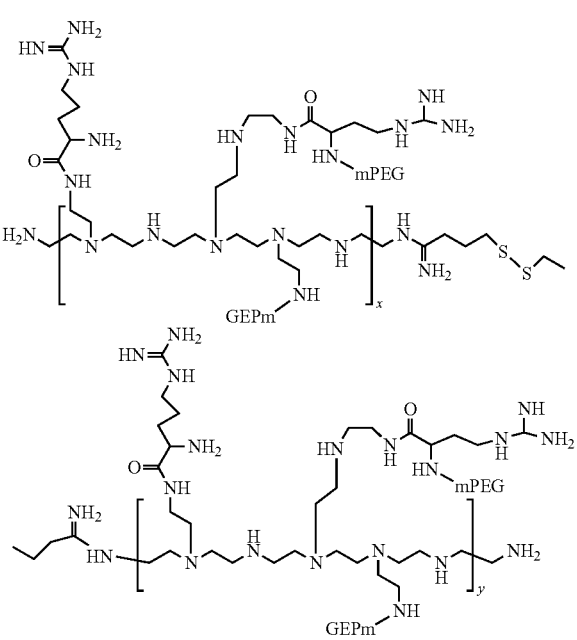

[Formula 2]

where each of x and y independently is an integer from 1 to 5.

2. A polymer-virus complex in which the polymer of Formula 2 of claim 1 is bound to a surface of a virus.

3. The polymer-virus complex of claim 2, wherein the virus is any one selected from the group consisting of adenovirus (Ads), adeno-associated virus (AAVs), retrovirus, lentivirus, herpes simplex virus and vaccinia virus.

4. The polymer-virus complex of claim 2, wherein the virus is an Ad.

5. A pharmaceutical composition, comprising:
   (a) the polymer-virus complex of claim 2; and
   (b) a pharmaceutically acceptable carrier.

6. The pharmaceutical composition of claim 5, wherein the composition further comprises a therapeutic gene.

7. The pharmaceutical composition of claim 5, wherein the virus is any one selected from the group consisting of adenovirus (Ads), adeno-associated virus (AAVs), retrovirus, lentivirus, herpes simplex virus and vaccinia virus.

8. The pharmaceutical composition of claim 5, wherein the virus is an Ad.

9. The pharmaceutical composition of claim 6, wherein the therapeutic gene is a cancer-treating gene selected from the group consisting of a drug-sensitizing gene, a tumor suppressor gene, an antigenic gene, a cytokine gene, a cytotoxic gene, a cytostatic gene, a pro-apoptotic gene, and an anti-angiogenic gene.

* * * * *